US010053741B2

(12) United States Patent
Yang et al.

(10) Patent No.: US 10,053,741 B2
(45) Date of Patent: Aug. 21, 2018

(54) HIV-1 GENOTYPING ASSAY FOR GLOBAL SURVEILLANCE OF HIV-1 DRUG RESISTANCE

(71) Applicant: The United States of America as represented by the Secretary of the Department of Health and Human Services, Washington, DC (US)

(72) Inventors: Chunfu Yang, Lilburn, GA (US); Zhiyong Zhou, Lilburn, GA (US); Nicholas Wagar, Decatur, GA (US); Joshua R. DeVos, Atlanta, GA (US)

(73) Assignee: The United States of America as represented by the Secretary of the Dept. of Health & Human Services, Washington, DC (US)

( * ) Notice: Subject to any disclaimer, the term of this patent is extended or adjusted under 35 U.S.C. 154(b) by 319 days.

(21) Appl. No.: 14/719,338

(22) Filed: May 22, 2015

(65) Prior Publication Data

US 2015/0267269 A1 Sep. 24, 2015

Related U.S. Application Data

(62) Division of application No. 14/125,564, filed as application No. PCT/US2012/045523 on Jul. 5, 2012, now Pat. No. 9,040,244.

(60) Provisional application No. 61/504,522, filed on Jul. 5, 2011.

(51) Int. Cl.
C12Q 1/70 (2006.01)

(52) U.S. Cl.
CPC ....... *C12Q 1/703* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,114,312 | A | 9/2000 | Liszewicz et al. |
| 6,803,187 | B1 | 10/2004 | Stuyver |
| 6,806,046 | B2 | 10/2004 | Johnston-Dow et al. |
| 6,852,491 | B2 | 2/2005 | Harris et al. |
| 2003/0148266 | A1 | 8/2003 | Hahn et al. |
| 2008/0318205 | A1 | 12/2008 | Biron et al. |
| 2009/0023164 | A1 | 1/2009 | Golding et al. |
| 2009/0226886 | A1 | 9/2009 | Mitsuhashi |
| 2009/0258342 | A1 | 10/2009 | Ducar et al. |
| 2014/0106340 | A1 | 4/2014 | Yang et al. |

FOREIGN PATENT DOCUMENTS

| EP | 0421109 A2 | 4/1991 |
| WO | WO 1999/067428 A2 | 12/1999 |
| WO | WO 2000/046403 A2 | 8/2000 |
| WO | WO 2002/070731 A2 | 9/2002 |
| WO | WO 2008/062385 A2 | 5/2008 |
| WO | WO 2008/115427 A2 | 9/2008 |
| WO | WO2010080582 | * 7/2010 | ............... C12Q 1/68 |

OTHER PUBLICATIONS

Genbank Accession No. AF033819.3—HIV-1, complete genome (GI: 4558520, submitted by Chappey et al. Nov. 12, 1997, retrieved on Mar. 10, 2017 from http://www.ncbi.nlm.nih.gov/nuccore/AF033819).*
Yang C, McNulty A, Diallo K, Zhang J, Titanji B, Kassim S, Wadonda-Kabondo N, Aberle-Grasse J, Kibuka T, Ndumbe PM, Vedapuri S, Zhou Z, Chilima B, Nkengasong JN. Development and application of a broadly sensitive dried-blood-spot-based genotyping assay for global surveillance of HIV-1 drug resistance. J Clin Microbiol. Sep. 2010; 48(9):3158-64.*
Gadberry MD, Malcomber ST, Doust AN, Kellogg EA. Primaclade—a flexible tool to find conserved PCR primers across multiple species. Bioinformatics. Apr. 1, 2005; 21(7):1263-4. Epub Nov. 11, 2004.*
Genbank Accession No. AF033819.3—HIV-1, complete genome (GI: 4558520, submitted by Chappey et al. Nov. 12, 1997, retrieved on May 1, 2014 from http://www.ncbi.nlm.nih.gov/nuccore/AF033819).*
Lowe T, Sharefkin J, Yang SQ, Dieffenbach CW. A computer program for selection of oligonucleotide primers for polymerase chain reactions. Nucleic Acids Res.Apr. 11, 1990; 18(7):1757-61.*
Yang C, McNulty A, Diallo K, Zhang J, Titanji B, Kassim S, Wadonda-Kabondo N, Aberle-Grasse J, Kibuka T, Ndumbe PM, Vedapuri S, Zhou Z, Chilima B, Nkengasong JN. Development and application of a broadly sensitive dried-blood-spot-based genotyping assay for global surveillance of HIV-1 drug resistance. J Clin Microbiol. Sep. 2010; 48(9):3158-64. Epub.*
Abbott Laboratories, "RealTime HIV-1," Abbot Molecular web site, http://www.abbottmolecular.com/RealTimeHIV1_22838.aspx (accessed May 22, 2010).
Abbott Laboratories, "Abbot Molecular ViroSeq HIV-1 Genotyping System," Abbott Molecular web site, http://www.abbottmolecular.com/ViroSeqHIV1GenotypingSystem_1079.aspx (accessed May 23, 2010).

(Continued)

*Primary Examiner* — Samuel C Woolwine
*Assistant Examiner* — Olayinka A Oyeyemi
(74) *Attorney, Agent, or Firm* — Klarquist Sparkman, LLP

(57) ABSTRACT

Provided herein are new methods, primers, and kits for genotyping HIV-1, including group M viral strains. The methods can be used for HIV-1 drug resistance surveillance and monitoring, for example in resource-poor countries. The disclosed methods can detected more mixed HIV-1 population than previous methods. Given the high efficiency in genotyping diverse HIV-1 group M viral strains from plasma and dried blood spot (DBS) samples and substantial reagent cost saving, the disclosed methods can be used for HIV-1 drug resistance genotyping in both antiretroviral therapy (ART)-naive and -experienced populations for surveillance purposes and patient monitoring.

19 Claims, 3 Drawing Sheets

(56) References Cited

OTHER PUBLICATIONS

Aghokeng et al., "High Failure Rate of ViroSeqTM HIV-1 Genotyping System for Drug Resistance Testing in Cameroon, a Context of Broad HIV-1 Genetic Diversity," *J. Clin. Microbiol.* doi:101128/JCM01478-10, 2011.

Aitken et al., "Development and Evaluation of an Assay for HIV-1 Protease and Reverse Transcriptase Drug Resistance Genotyping of all Major Group-M Subtypes," *J. Clin. Virol.* 54:21-25, 2012.

Avert, "HIV types, subtypes, groups and strains," Avert.org web site, http://www.avert.org/hiv-types.htm (accessed May 21, 2010).

Ayele, et al., "Surveillance Technology for HIV-1 Subtype C in Ethiopia: an Env-Based NASBA Molecular Beacon Assay to Discriminate Between Subcluster C and C'," *J. Virol. Methods* 130:22-29, 2005.

Beddows et al., "Performance of Two Commercially Available Sequence-Based HIV-1 Genotyping Systems for the Detection of Drug Resistance Against HIV Type 1 Group M Subtypes," *J. Med. Virol.* 70:337-342, 2003.

Bennett, "The Requirement for Surveillance of HIV Drug Resistance Within Antiretroviral Rollout in the Developing World," *Curr. Opin. Infect. Dis.* 19:607-614, 2006.

BioMed Central Ltd., "Using Genomic Signatures for HIV-1 Sub-Typing," BioMed Central web site, http://www.biomedcentral.com/1471-2105/11/S1/S26 (accessed May 22, 2010).

Bio-Rad Laboratories, Inc., "Genscreen ULTRA HIV Ag Ab Assay," Bio-Rad web site, http://www.bio-rad.com/evportal/evolutionPortal.portal?_nfpb=true&_pageLabel=search_page&sfMode=search&sfStartNumber=1&clearQR=true&isMainSearch=true&js=1&searchString=GS%20HIV%20Combo%20Ag%2FAb%20EIA&database=productskus+productcategories+productdetails+msds+literatures+inserts+faqs+downloads+webpages+assays+genes+pathways+plates+promotions&tabName=DIVISIONNAME (accessed Nov. 22, 2013).

Buckton, "New Methods for the Surveillance of HIV Drug Resistance in the Resource Poor World," *Curr. Opin. Infect. Dis.* 21:653-658, 2008.

Buckton et al., "Development and Optimization of an Internally Controlled Dried Blood Spot Assay for Surveillance of Human Immunodeficiency Virus Type-1 Drug Resistance," *J. Antimicrob. Chemother.* 62:1191-1198, 2008.

Chen et al., "Evaluation of an In-House Genotyping Resistance Test for HIV-1 Drug Resistance Interpretation and Genotyping," *J. Clin. Virol.* 39:125-131, 2007.

Eshleman et al., "Characterization of Nevirapine Resistance Mutations in Women With Subtype A Vs. D HIV-1 6-8 Weeks After Single-Dose Nevirapine (HIVNET 012)," *J. Acquir. Immune Defic. Syndr.* 35:126-130, 2004.

Eshleman et al., "Performance of the Celera Diagnostics ViroSeq HIV-1 Genotyping System for Sequence-Based Analysis of Diverse Human Immunodeficiency Virus Type 1 Strains," *J. Clin. Microbiol.* 42:2711-2717, 2004.

Eshleman et al., "Sensitivity and Specificity of the ViroSeq Human Immunodeficiency Virus Type 1 (HIV-1) Genotyping System for Detection of HIV-1 Drug Resistance Mutations by Use of an ABI PRISM 3100 Genetic Analyzer," *J. Clin. Microbiol.* 43:813-817, 2005.

Eshleman et al., "Analysis of pol Integrase Sequences in Diverse HIV Type 1 Strains Using a Prototype Genotyping Assay," *AIDS Res. Hum. Retroviruses* 25:343-345, 2009.

Fontaine et al. "Evaluation of Two Commercial Kits for the Detection of Genotypic Drug Resistance on a Panel of HIV Type 1 Subtypes A through J," *J. Acquir. Immune Defic. Syndr.* 28:254-258, 2001.

Galli et al., "Sources and Magnitude of Intralaboratory Variability in a Sequence-based Genotypic Assay for Human Immunodeficiency Virus Type 1 drug Resistance," *J Clin Microbiol* 41:2900-2907, 2003.

Genbank Accession No. AF033819, Aug. 28, 2002.

Gilks et al., "The WHO public-health approach to antiretroviral treatment against HIV in resource-limited settings," *Lancet* 368:505-510, 2006.

Global Business Coalition on HIF/AIDS, "HIV/AIDS Testing Market to Exceed $3.9 Billion by 2015, According to New Report by Global Industry Analysts, Inc.," Global Business Coalition on HIV/AIDS, Tuberculosis and Malaria web site http://www.prweb.com/releases/HIV_AIDS_testing/screening_monitoring_test/prweb1509864.htm (accessed Nov. 22, 2013).

Hearps et al., "An HIV-1 Integrase Genotype Assay for the Detection of Drug Resistance Mutations," *Sex. Health.* 6:305-309, 2009.

Hearps et al., "Stability of Dried Blood Spots for HIV-1 Drug Resistance Analysis," *Curr. HIV Res.* 8:134-140, 2010.

Hirsch et al., "Antiretroviral Drug Resistance Testing in Adult HIV-1 Infection: 2008 Recommendations of an International AIDS Society—USA panel," *Clin. Infect. Dis.* 47:266-285, 2008.

Jagodzinski et al., "Performance Characteristics of Human Immunodeficiency Virus Type 1 (HIV-1) Genotyping Systems in Sequence-Based Analysis of Subtypes Other than HIV-1 Subtype B," *J. Clin. Microbiol.* 41:998-1003, 2003.

Kijak et al., "Development and Application of a High-Throughput HIV Type 1 Genotyping Assay to Identify CRF02_AG in West/West Central Africa," *AIDS Res. Hum. Retroviruses* 20:521-530, 2004.

Kijak et al., "Distinguishing Molecular Forms of HIV-1 in Asia with a High-Throughput, Fluorescent Genotyping Assay, MHAbce v.2," *Virology* 358:178-191, 2007.

Laboratory Corporation of America, "GenoSure," LabCorp web site, https://www.labcorp.com/wps/portal/!ut/p/c0/04_SB8K8xLLM9MSSzPy8xBz9CP0os_hQV5NgQ09LYwODQ-GM3A08zdwN_X8swQzMPc_2CbEdFAPTqc3Y!/?WCM_PORTLET=PC_7_UE4S1I9300Q3F0I6G0OM9V16P4_WCM&WCM_GLOBAL_CONTEXT=/wps/wcm/connect/labcorp+content/LabCorp/Education+and+Research/Research/Virology/Human+Immunodeficiency+Virus/HIV+Resistance/GenoSure, (accessed Dec. 11, 2013).

Lowe et al., "A Computer Program for Selection of Oligonucleotide Primers for Polymerase Chain Reactions," *Nucl Acids Res.* 18:1757-1761, 1990.

McNulty et al., "Development and Application of a Broadly Sensitive Genoytyping Assay for Surveillance of HIV-1 Drug Resistance in PEPFAR Countries," *Antivir. Ther.* 13:a117, Abstract 107, presented at the XVII International HIV Drug Resistance Workshop: Basic Principles & Clinical Implications, Sitges, Spain, Jun. 10-14, 2008.

Mracna et al., "Performance of Applied Biosystems ViroSeq HIV-1 Genotyping System for Sequence-Based Analysis of Non-Subtype B Human Immunodeficiency Virus Type 1 From Uganda," *J. Clin. Microbiol.* 39:4323-4327, 2001.

Raymond et al., "Prediction of HIV Type 1 Subtype C Tropism by Genotypic Algorithms Built from Subtype B Viruses," *J. Acquir. Immune Defic. Syndr.* 53:167-175, 2010.

Reuters, "HIV/AIDS Research Network Recommends Use of Abbott RealTime Viral Load Test for NIH-Sponsored Clinical Trials," Reuters press release, http://www.reuters.com/article/2009/05/07/idUS182343+07-May-2009+PRN20090507 (accessed Dec. 11, 2013).

Robinson, John, "Rising Prevalence of Variant HIV-1 Subtypes Poses New Diagnostic Challenge," *MLO Med Lab Obs.* 39:28, 30, 2007.

Rottinghaus et al., "Dried Blood Spot Specimens are a Suitable Alternative Sample Type for HIV-1 Viral Load Measurement and Drug Resistance Genotyping in Patients Receiving First-Line Antiretroviral Therapy," *Clin. Infect. Dis.* 54:1187-1195, 2012.

Saravanan et al., "Evaluation of Two Human Immunodeficiency Virus-1 Genotyping Systems: ViroSeq 2.0 and an In-House Method," *J. Virol. Methods* 159:211-216, 2009.

Schuurman et al., "Worldwide Evaluation of DNA Sequencing Approaches for Identification of Drug Resistance Mutations in the Human Immunodeficiency Virus Type 1 Veverse Transcriptase," *J. Clin. Microbiol.* 37:2291-2296, 1999.

Siemens AG, "Trugene HIV-1 Genotyping Assay," Siemens web site, http://www.healthcare.siemens.com/molecular-diagnostics/

(56) References Cited

OTHER PUBLICATIONS molecular-diagnostics-in-vitro-diagnostics/trugene-hiv-1-genotyping-assay (accessed Dec. 11, 2013).
Terra Daily, "HIV Market to Top 10 Billion Dollars," Terra Daily web site, http://www.terradaily.com/reports/HIV_Market_To_Top_10_Billion_Dollars_999.html (accessed May 22, 2010).
Time, Inc., "New Study Raises Concerns About HIV-Drug Resistance," Time.com web site, http://www.time.com/time/health/article/0,8599,1953718,00.html (accessed May 23, 2010).
U.S. Food and Drug Administration, "Visible Genetics 510(k) summary," U.S. Food and Drug Administration web site, http://www.fda.gov/downloads/BiologicsBloodVaccines/BloodBloodProducts/ApprovedProducts/SubstantiallyEquivalent510kDeviceInformation/UCM088974.pdf (accessed May 23, 2010).
Vega et al., "Oligonucleotide Ligation Assay for Detection of Mutations Associated with Reverse Transcriptase and Protease Inhibitor Resistance in Non-B Subtypes and Recombinant Forms of Human Immunodeficiency Virus Type 1," *J. Clin. Microbiol.* 43:5301-5304, 2005.
Wallis et al., "Affordable In-House Antiretroviral Drug Resistance Assay With Good Performance in Non-Subtype B HIV-1," *J. Virol. Methods* 163:505-508, 2010.
WHO (2010) WHO HIVResNet HIV Drug Resistance Laboratory Strategy. www.WHO.int/hiv/topics/drugresistance, Jul. 2010.
WHO (2010) WHO Manual for HIV Drug Resistance Testing Using Dried Blood Spot Specimens. www.WHOint/hiv/topics/drugresistance.
Yang et al., "Development and Application of a Broadly Sensitive Dried-Blood-Spot-Based Genotyping Assay for Global Surveillance of HIV-1 Drug Resistance," *J. Clin. Microbiol.* 48:3158-3164, 2010.
Zhou et al., "Optimisation of a Low Cost and Broadly Sensitive Genotyping Assay for HIV-1 Drug Resistance of Surveillance and Monitoring in Resource-Limited Settings," *PLoS One* 6:e28184, 2011.
Ziemniak et al., "A Sensitive Genotyping Assay for Detection of Drug Resistance Mutations in Reverse Transcriptase of HIV-1 Subtypes B and C in Samples Stored as Dried Blood Spots or Frozen RNA Extracts," *J. Virol. Methods* 136:238-247, 2006.
Database Geneseq [Online], "Hybridisation primer RT-F8 specific for HXB2 pol gene," retrieved from EBI accession No. GSN:AAA72762, Database Accession No. AAA72762, Sep. 15, 2003.
Database Geneseq [Online], "PCR primer RT-R6 for HXB2 pol gene," retrieved from EBI Accession No. GSN:AAV45623, Database Accession No. AAV45623, Mar. 4, 1999.
Database Geneseq [Online], "HIV gag gene forward PCR primer HRM-3F," retrieved from EBI Accession No. GSN:AZH55872, Database Accession No. AZH55872, Jun. 9, 2011.
Database Geneseq [Online], "HIV gag gene PCR primer Pr1 forward," retrieved from Ebi Accession No. GSN:AZH55886, Database Accession No. AZH55886, Jun. 9, 2011.
Database Geneseq [Online], "Modified internal coding region of HIV gag/pol polyprotein," retrieved from EBI Accession No. GSN:AAQ11607, Database Accession No. GSN:AAQ11607, Jan. 9, 2003.
EP 12808072.8 Examination Report dated Jan. 16, 2017 (5 pages).
Thermo Fisher Scientific Inc., "HIV-1 Genotyping Workflow User Guide," Catalog Nos. A32317 and A32318, Publication No. MAN0016022, 2017 (35 pages).
Thermo Fisher Scientific Inc., "One Step Closer to Realizing the 90-90-90 Target," Flyer, 2016.
Towler et al., "Analysis of HIV diversity using a high-resolution melting assay," *AIDS Research and Human Retroviruses* 26:913-918, 2010.
CA 2,838,091 Examination Report dated Mar. 2, 2018 (5 pages).

\* cited by examiner

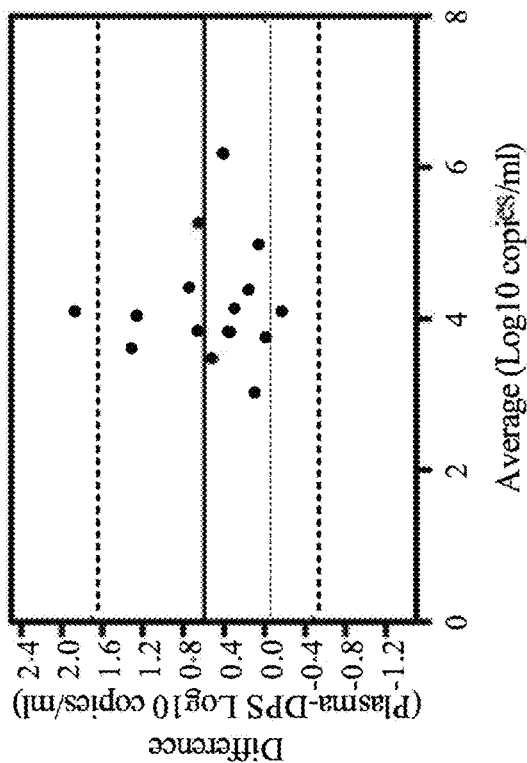
FIG. 3B  DPS
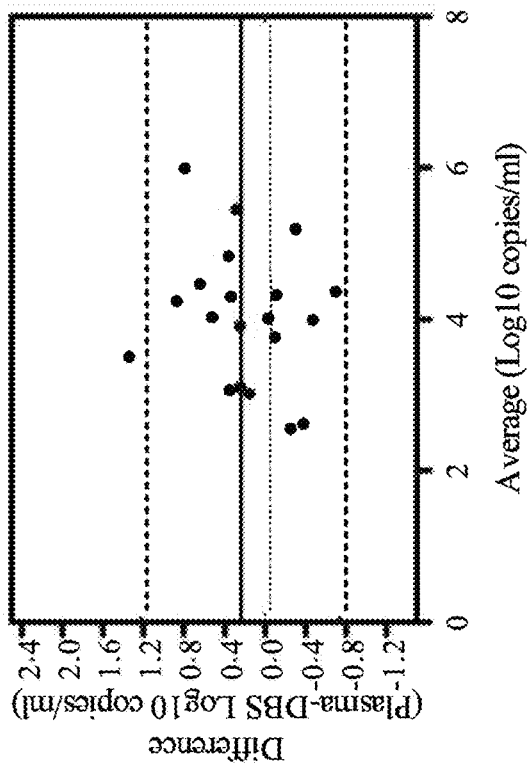
FIG. 3A  DBS

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: forward primer to amplify HIV-1 pol using
      RT-PCR
<220> FEATURE:
<221> NAME/KEY: misc_feature
<222> LOCATION: (5)..(5)
<223> OTHER INFORMATION: R is A or G
<220> FEATURE:
<221> NAME/KEY: modified_base
<222> LOCATION: (8)..(8)
<223> OTHER INFORMATION: n is inosine
<220> FEATURE:
<221> NAME/KEY: misc_feature
<222> LOCATION: (11)..(11)
<223> OTHER INFORMATION: Y is C or T
<220> FEATURE:
<221> NAME/KEY: misc_feature
<222> LOCATION: (17)..(17)
<223> OTHER INFORMATION: R is A or G
<220> FEATURE:
<221> NAME/KEY: misc_feature
<222> LOCATION: (20)..(20)
<223> OTHER INFORMATION: R is A or G

<400> SEQUENCE: 1
tgaargantg yactgaragr caggctaat                                    29

<210> SEQ ID NO 2
<211> LENGTH: 25
<212> TYPE: DNA
<213> ORGANISM: Artificial Sequence
<220> FEATURE:
<223> OTHER INFORMATION: forward primer to amplify HIV-1 pol using
      RT-PCR
<220> FEATURE:
<221> NAME/KEY: misc_feature
<222> LOCATION: (6)..(6)
<223> OTHER INFORMATION: R is A or G

<400> SEQUENCE: 2
actgaragrc aggctaattt tttag                                        25

<210> SEQ ID NO 3
<211> LENGTH: 20
<212> TYPE: DNA
<213> ORGANISM: Artificial Sequence
<220> FEATURE:
<223> OTHER INFORMATION: forward primer to amplify HIV-1 pol using
      RT-PCR
<220> FEATURE:
<221> NAME/KEY: misc_feature
<222> LOCATION: (7)..(7)
<223> OTHER INFORMATION: R is A or G
<220> FEATURE:
<221> NAME/KEY: misc_feature
<222> LOCATION: (11)..(11)
<223> OTHER INFORMATION: Y is C or T

<400> SEQUENCE: 3
```
tagggaraat ytggccttcc                                              20

<210> SEQ ID NO 4
<211> LENGTH: 23
<212> TYPE: DNA
<213> ORGANISM: Artificial Sequence
<220> FEATURE:
<223> OTHER INFORMATION: reverse primer to amplify HIV-1 pol using
      RT-PCR

<400> SEQUENCE: 4
atccctgcat aaatctgact tgc                                          23

<210> SEQ ID NO 5
<211> LENGTH: 24
<212> TYPE: DNA
<213> ORGANISM: Artificial Sequence
<220> FEATURE:
<223> OTHER INFORMATION: forward primer to amplify HIV-1 pol using
      nested PCR
<220> FEATURE:
<221> NAME/KEY: misc_feature
<222> LOCATION: (6)..(6)
<223> OTHER INFORMATION: R is A or G
<220> FEATURE:
<221> NAME/KEY: misc_feature
<222> LOCATION: (16)..(16)
<223> OTHER INFORMATION: R is A or G

<400> SEQUENCE: 5
ctttarcttc cctcaratca ctct                                         24

<210> SEQ ID NO 6
<211> LENGTH: 23
<212> TYPE: DNA
<213> ORGANISM: Artificial Sequence
<220> FEATURE:
<223> OTHER INFORMATION: reverse primer to amplify HIV-1 pol using
      nested PCR

<400> SEQUENCE: 6
cttctgtatg tcattgacag tcc                                          23

<210> SEQ ID NO 7
<211> LENGTH: 22
<212> TYPE: DNA
<213> ORGANISM: Artificial Sequence
<220> FEATURE:
<223> OTHER INFORMATION: primer to sequence HIV-1 pol
<220> FEATURE:
<221> NAME/KEY: misc_feature
<222> LOCATION: (12)..(12)
<223> OTHER INFORMATION: R is A or G
<220> FEATURE:
<221> NAME/KEY: misc_feature
<222> LOCATION: (18)..(18)
<223> OTHER INFORMATION: R is A or G

<400> SEQUENCE: 7
agtcctattg aractgtrcc ag                                           22

<210> SEQ ID NO 8
<211> LENGTH: 21
<212> TYPE: DNA
<213> ORGANISM: Artificial Sequence
<220> FEATURE:
<223> OTHER INFORMATION: primer to sequence HIV-1 pol
<220> FEATURE:
<221> NAME/KEY: misc_feature
<222> LOCATION: (4)..(4)

-continued

```
<223> OTHER INFORMATION: Y is C or T

<400> SEQUENCE: 8
tttytcttct gtcaatggcc a                                              21

<210> SEQ ID NO 9
<211> LENGTH: 21
<212> TYPE: DNA
<213> ORGANISM: Artificial Sequence
<220> FEATURE:
<223> OTHER INFORMATION: primer to sequence HIV-1 pol
<220> FEATURE:
<221> NAME/KEY: misc_feature
<222> LOCATION: (17)..(17)
<223> OTHER INFORMATION: R is A or G
<220> FEATURE:
<221> NAME/KEY: misc_feature
<222> LOCATION: (20)..(20)
<223> OTHER INFORMATION: Y is C or T

<400> SEQUENCE: 9
cagtactgga tgtgggrgay g                                              21

<210> SEQ ID NO 10
<211> LENGTH: 22
<212> TYPE: DNA
<213> ORGANISM: Artificial Sequence
<220> FEATURE:
<223> OTHER INFORMATION: primer to sequence HIV-1 pol

<400> SEQUENCE: 10
tactaggtat ggtaaatgca gt                                             22
```

HIV-1 GENOTYPING ASSAY FOR GLOBAL SURVEILLANCE OF HIV-1 DRUG RESISTANCE

CROSS-REFERENCE TO RELATED APPLICATIONS

This application is a divisional of U.S. application Ser. No. 14/125,564, filed Dec. 11, 2013, now U.S. Pat. No. 9,040,244, which is the U.S. National Stage of International Application No. PCT/US2012/045523, filed Jul. 5, 2012, which was published in English under PCT Article 21(2), which in turn claims the benefit of U.S. Provisional Application No. 61/504,522 filed on Jul. 5, 2011. All of the prior applications are incorporated herein by reference in their entirety.

FIELD

This application relates to nucleic acid primers and methods of their use to genotype HIV-1 M subtypes, circulating recombinant forms (CRFs) and unique recombinant forms (URFs). Such methods can be used for surveillance of HIV-1 drug resistance and monitoring patients on antiretroviral therapy, for example by detecting resistance mutations in the protease and reverse transcriptase gene of the HIV-1 pol gene region.

BACKGROUND

Treatment of HIV-1 infection with highly active antiretroviral therapy (HAART) in the past decades has remarkably reduced HIV/AIDS related mortality and morbidity. However, the emergence of drug resistance in persons on antiretroviral therapy (ART) and the transmission of drug-resistant HIV strains to newly infected persons are a major threat to the global effort for HIV prevention and treatment success [1,2,3]. Recently, access to antiretroviral drugs (ARVs) has been scaled up rapidly in resource-limited countries where availability of laboratory monitoring is often limited or lacking [4,5]. This creates the potential for HIVDR emergence and transmission in these settings. Detection and monitoring of HIVDR by molecular genotyping is pivotal to ensure ongoing regimen efficacy. It is the standard of care in resource-rich countries [2,6]; however in resource poor countries, HIVDR testing is not generally available or it is too costly to be used in routine monitoring of patients receiving ARVs. Therefore, the World Health Organization (WHO) recommends population-based surveillance and monitoring of drug resistance (DR) in resource-limited settings [2,4,7]. Pattern and rates of transmitted and acquired drug resistant HIV variants will collectively inform regional and global recommendations on which ARVs to maintain or change in treatment regimens [7].

Population sequencing-based genotyping methods including ViroSeq, TRUGENE and in-house assays are widely used and the most informative and affordable genotyping methods for monitoring patients on ART in clinical practice [8,9,10,11]. However, ViroSeq and TRUGENE, the two FDA-approved genotyping assays were designed for HIV-1 subtype B viruses which are the predominant HIV-1 strains in resource-rich countries. In addition, these commercial kits are expensive and less sensitive to non-B subtypes, limiting the application in resource-limited settings [12,13,14]. There have been no commercially available HIV-1 genotyping assays designed for non-B subtypes and CRFs that are predominant viral strains in resource-limited countries. Moreover, the demand for low cost and sensitive genotyping methods is increasing with the establishment and expansion of laboratory molecular monitoring in these settings [15,16].

The most frequently used HIVDR genotypic assays are assays that detect resistance mutations in the reverse-transcriptase (RT) and protease (PR) genes [17,18,19]. The minimal genotyping requirements for these two regions are PR codons 10-99 and RT codons 41-240 [3,20,21]. An original in-house assay [22] had limitations: (1) it does not cover the entire PR gene region required for resistance testing; and (2) for some HIV-1 subtypes or CRFs, some sequencing primers generate higher background noise which affected the detection of mixture bases. Thus, a new assay is needed.

In-house assays are relatively inexpensive and sensitive for multiple subtypes, but in-house assays should only be implemented after adequate validation, including evaluating assay's performance with various HIV-1 subtypes [3,20,23]. Factors that could contribute to genotyping quality include type of assay/kit used, specimen handling and storage, level of experience of technicians performing the analysis, heterozygosity of sequences, and viral subtypes in clinical samples [11,21].

SUMMARY

The present disclosure provides methods for genotyping HIV-1. The inventors have identified primers that can be used to genotype HIV-1, including subtypes of group M (for example subtypes A, B, C, D, F, G, H, J, K and circulating recombinant forms [CRFs] and unique recombinant forms [URFs]). In one example, the HIV-1 is a non-B subtype (for example subtype A, C, D, F, G, H, J, K, CRFs or URFs). Genotyping of HIV-1 pol gene region can be used to determine if a patient has one or more HIV-1 drug resistant (HIVDR) mutations, such as HIVDR mutations in protease (PR) and reverse transcriptase (RT) regions of the HIV-1 pol gene. In some examples, the disclosed methods permit detection of a new HIVDR mutation, for example a new HIVDR mutation in a population. In particular examples, the method has a specificity of at least 99%, such as at least 99.5%, and/or a sensitivity of at least 95% (such as at least 96%, at least 98%, or as at least 99%).

In particular examples, the method includes contacting a sample obtained from a subject with a first forward nucleic acid primer (also referred to herein as a degenerate oligonucleotide or primer) that includes or consists of the sequence shown in SEQ ID NO: 1 and 2 (such as a sequence comprising at least 90% sequence identity to SEQ ID NO: 1 and 2) or SEQ ID NO: 3 (such as a sequence comprising at least 90% sequence identity to SEQ ID NO: 3) and a first reverse nucleic acid primer that includes or consists of the sequence shown in SEQ ID NO: 4 (such as a sequence comprising at least 90% sequence identity to SEQ ID NO: 4), thereby generating a first reaction mixture. The first reaction mixture is subjected to conditions that permit amplification of a portion of HIV-1 pol in the sample (for example using reverse transcription polymerase chain reaction (RT-PCR)), thereby generating a first amplification product (such as an RT-PCR product). The first amplification product (such as an RT-PCR product) product can be sequenced (for example using any of SEQ ID NOS: 5-10), thereby determining the genotype of HIV-1 in the sample. In some examples, the method further includes contacting the first amplification product (such as an RT-PCR product) with a second forward nucleic acid primer that includes or consists of the sequence shown in SEQ ID NO: 5 (such as a sequence comprising at least 90% sequence identity to SEQ ID NO: 5) and a second reverse nucleic acid primer that includes or consists of the sequence shown in SEQ ID NO: 6 (such as a sequence comprising at least 90% sequence identity to SEQ ID NO: 6), thereby generating a second reaction mixture. The second reaction mixture is subjected to a second amplification reaction (such as nested PCR) under conditions sufficient to amplify a region of HIV-1 pol that includes PR and RT gene regions, thereby generating a second amplification product (such as a nested PCR product). The second amplification product (such as a nested PCR product) is sequenced (for example using SEQ ID NOS: 5-10 or a sequence comprising at least 90% sequence identity to any of SEQ ID NOS: 5-10) thereby determining the genotype of HIV-1 in the sample.

In some examples, the method further includes comparing the sequence of the first amplification product (such as an RT-PCR product) and/or second amplification product (such as a nested PCR product) to the WHO surveillance drug resistance mutation (SDRM) list or the International AIDS Society (IAS) HIV drug resistance mutation list (see for example Johnson et al., *Top. HIV Med.* 18:156-63, 2010), wherein the presence of a mutation can determine if the subject will be or is resistant to HIV-1 therapeutics. In some examples, the methods can also include determining the HIV-1 viral load (VL) in the subject. The determination of HIV-1 genotype can be used to determine the anti-HIV-1 therapy that the patient should receive. In some examples, the first amplification product (such as an RT-PCR product) and or nested PCR product can be purified prior to sequencing or detection of HIVDR mutations using allele-specific techniques.

In some examples, HIV-1 genotyping is performed using HIV-1 DNA obtained from peripheral blood mononuclear cells (PBMC). In such examples, the RT amplification step can be omitted. For example, the HIV-1 DNA can be incubated with a forward nucleic acid primer that includes or consists of the sequence shown in SEQ ID NO: 1 and 2, 3, or 5 (such as a sequence comprising at least 90% sequence identity to SEQ ID NO: 1 and 2, 3, or 5) and a reverse nucleic acid primer that includes or consists of the sequence shown in SEQ ID NO: 4 or 6 (such as a sequence comprising at least 90% sequence identity to SEQ ID NO: 4 or 6), thereby generating a reaction mixture. The reaction mixture is incubated under conditions sufficient to amplify a portion of HIV-1 pol comprising HIV-1 RT and PR, thereby generating an amplification product. The resulting amplification product is sequenced to determine the genotype of HIV-1 or detected by allele-specific techniques.

One skilled in the art will appreciate that the disclosed methods can be used with primers having minor variations of any of SEQ ID NOS: 1-10, such as sequences having at least 90%, at least 95%, at least 97%, at least 98% or at least 99% sequence identity to any of SEQ ID NOS: 1-10. In some examples, such variant primers are 18 to 32 nucleotides (nt) in length.

The disclosure also provides primers (also referred to herein as degenerate oligonucleotides) and compositions that include such primers, which can be used with the disclosed methods. For example, the disclosure provides a primer consisting of the nucleic acid sequence shown in any of SEQ ID NOS: 1-10, as well as sequences having at least 90%, at least 95%, at least 97%, at least 98% or at least 99% sequence identity to any of SEQ ID NOS: 1, 2, 3, 4, 5, 6, 7, 8, 9, or 10, that are 18 to 32 nucleotides in length, such as 19 to 30, 20 to 29, or 20 to 30 nucleotides in length. Such primers can also include a label.

Kits that include one or more of the disclosed primers are also encompassed by this disclosure. In a particular example, the kit includes 1, 2, 3, 4, 5, 6, 7, 8, 9, or 10, of the disclosed primers (SEQ ID NOS: 1-10). In some examples, the kit can include one or more agents used to isolate nucleic acid molecules (such as RNA), one or more agents used to reverse transcribe RNA to cDNA, one or more agents for amplification of cDNA (such as for RT-PCR), one or more reagents for sequencing a nucleic acid molecule, or combinations thereof. In some examples, such kits also include materials for collecting a blood sample.

The foregoing and other objects and features of the disclosure will become more apparent from the following detailed description, which proceeds with reference to the accompanying figures.

BRIEF DESCRIPTION OF THE DRAWINGS

FIGS. 3A-3B are plots showing Bland-Altman analysis of DBS and DPS viral load compared to plasma. Nucleic acid was extracted from DBS, plasma, and DPS specimens using the NucliSens® EasyMag automated system and NucliSens® HIV-1 v1.1 RUO kits were used to determine the HIV-1 viral load using the NucliSens® EasyQ analyzer. All viral load values were normalized to a volume of 1 ml and DBS were further normalized for a chosen mean hematocrit of 40%. (A) DBS (n=20) or (B) DPS (n=16) specimens with a detectable viral load in both plasma and dried fluid spot specimens. The solid line represents the mean difference between plasma and DBS [0.23±0.50 (0.005 to 0.473)] or DPS [0.59±0.55 (0.299 to 0.880], and the dotted lines represent the 95% limits of agreement (mean difference±1.96×standard deviation) for DBS (−0.74 & 1.22, width 1.96) and DPS (−0.48 & 1.66, width 2.14).

SEQUENCE LISTING

Figure 1:
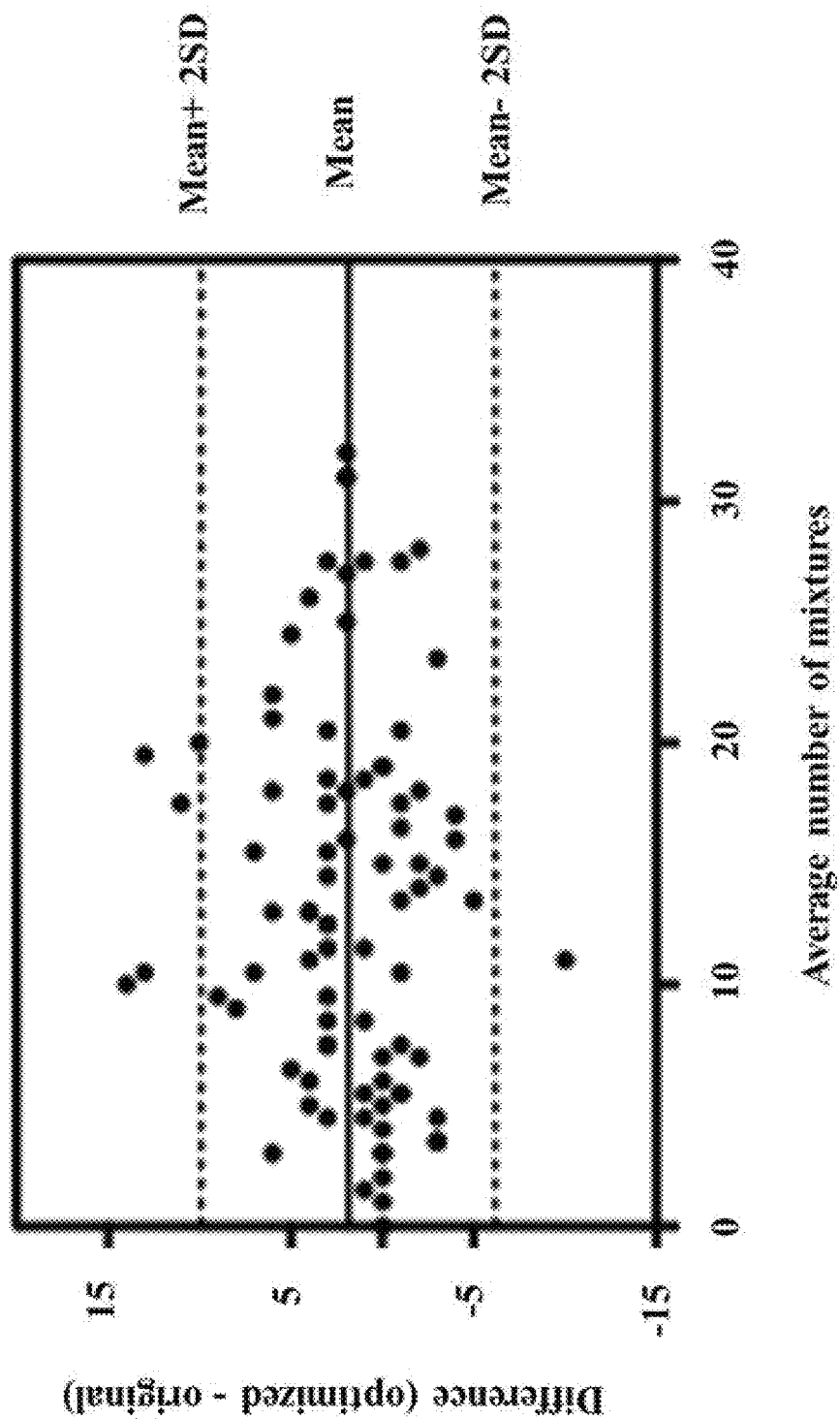
FIG. 1 is a plot showing the agreement of nucleotide mixtures called by the disclosed and original in-house assays from 87 samples detected by using ReCall program (minor base calling was set at ≥15% of major base). The agreement between these two assays was measured by the Bland and Altman analysis. X axis is the average of mixture number and Y axis is the difference between two assays.

The nucleotide sequences of the nucleic acids described herein are shown using standard letter abbreviations for nucleotide bases. Only one strand of each nucleic acid sequence (from 5'→3') is shown, but the complementary strand is understood as included by any reference to the displayed strand. Standard IUB nucleotide ambiguity codes are used: R=A or G; S=C or G; Y=C or T; W=A or T; M=A or C; and H=A, C, or T. It is noted that I is inosine (shown as "n" in SEQ ID NO: 1).

SEQ ID NOS: 1-3 are nucleic acid sequences of exemplary forward primers that can be used to amplify HIV-1 pol using RT-PCR or PCR.

SEQ ID NO: 4 is a nucleic acid sequence of exemplary reverse primer that can be used to amplify HIV-1 pol using RT-PCR or PCR.

SEQ ID NO: 5 is a nucleic acid sequence of exemplary forward primer that can be used to amplify HIV-1 pol using PCR or nested PCR and can be used for sequencing.

SEQ ID NO: 6 is a nucleic acid sequence of exemplary reverse primer that can be used to amplify HIV-1 pol using PCR or nested PCR and can be used for sequencing.

SEQ ID NOS: 7-10 are nucleic acid sequences of exemplary primers that can be used to sequence HIV-1 pol.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a primer" includes single or plural mutations and is considered equivalent to the phrase "comprising at least one mutation." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references and GenBank numbers cited herein are incorporated by reference (for GenBank numbers, those sequences present on GenBank on Jul. 5, 2011 are incorporated by reference).

ART: antiretroviral therapy
ARV: antiretroviral drug
CRF: circulating recombinant form
DBS: dried blood spot
DPS: dried plasma spot
DR: drug resistant
HIV-1: human immunodeficiency virus-1
nt: nucleotide
PCR: polymerase chain reaction
RT-PCR: reverse transcription PCR
PR: protease
RT: reverse transcriptase
VL: viral load Acquired immune deficiency syndrome or acquired immunodeficiency syndrome (AIDS or Aids): A collection of symptoms and infections resulting from injury to the immune system caused by HIV in humans, and similar viruses in other species (e.g., SIV and FIV).

Amino acid substitution: The replacement of one amino acid in peptide (such as in an HIV-1 PR or RT protein) with a different amino acid.

Amplifying a nucleic acid molecule: To increase the number of copies of a nucleic acid molecule, for example using PCR. The resulting amplification products are called "amplicons."

An example of in vitro amplification is the polymerase chain reaction (PCR), in which a nucleic acid molecule, such as cDNA reverse transcribed from RNA extracted from a biological sample obtained from a subject, is contacted with a pair of oligonucleotide primers, under conditions that allow for hybridization of the primers to the nucleic acid molecule (such as HIV-1 RNA). The primers are extended under suitable conditions, dissociated from the template, and then re-annealed, extended, and dissociated to amplify the number of copies of the nucleic acid molecule. Other examples of in vitro amplification techniques include real-time PCR, reverse transcription PCR (RT-PCR), quantitative real-time PCR, reverse transcriptase semi-nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antiretroviral therapy (ART): A treatment that can suppress or inhibit a retrovirus, such as HIV. In some examples such a treatment substantially reduces or inhibits retroviral replication or infection in a mammalian cell. In particular examples, includes agents that interfere with either host or viral mechanisms necessary for the formation or replication of a retrovirus in a mammal, such as one or more NNRTIs (e.g., efavirenz, nevirapine or delavirdine), NRTIs (e.g., lamuvidine and zidovudine), protease inhibitors, fusion inhibitors, RNAse H inhibitors, maturation inhibitors, portmanteau inhibitors, and integrase inhibitors.

Complementary: Complementary binding occurs when the base of one nucleic acid molecule forms a hydrogen bond to the base of another nucleic acid molecule. For example, complementary binding normally occurs between a probe (such as any of SEQ ID NOS: 1-10) to an HIV-1 nucleic acid molecule (such as an HIV-1 RT or PR sequence). However, nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Contacting: Placement in direct physical association; includes both in solid and liquid form. For example, contacting can occur in vitro with isolated nucleic acid molecules in solution.

Detect: To determine the existence or presence of, for example to determine whether a subject has an HIV-1 drug resistance mutation in the HIV-1 PR or RT gene. For example, detection can include determining the nucleic acid sequence of HIV-1 PR and/or RT (or portion thereof known to result in HIV-1 drug resistance) in a sample.

Fluorophore: A chemical compound, which when excited by exposure to a particular stimulus such as a defined wavelength of light, emits light (fluoresces), for example at a different wavelength. The disclosed primers can be labeled with a fluorophore.

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules eliminates the need for an external source of electromagnetic radiation, such as a laser. Examples of chemiluminescent molecules include, but are not limited to, aequorin.

Examples of particular fluorophores that can be used in the methods disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, Yakima Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores known to those skilled in the art can also be used, for example those available from Molecular Probes (Eugene, Oreg.).

Genotyping: To determine the genes of an organism, such as HIV-1. In a particular example, includes determining HIV-1 PR or RT genes. For example, genotyping can include determining the nucleic acid sequence of HIV-1 PR and/or RT (or portion of the gene that results in HIV-1 drug resistance when mutated). Exemplary methods of genotyping include polymerase chain reaction (PCR), DNA sequencing, allele specific oligonucleotide (ASO) probes, and hybridization to DNA microarrays or beads.

Highly active antiretroviral therapy (HAART): A treatment that includes a combination of several (such as two, three, four, five or more) anti-retroviral agents, thereby suppressing or inhibiting a retrovirus, such as HIV. Particular HAART therapies currently in use include (i) efavirenz+zidovudine+lamivudine; (ii) efavirenz+tenofovir+emtricitabine; (iii) lopinavir boosted with ritonavir+zidovudine+lamivudine; and (iv) lopinavir boosted with ritonavir+tenofovir+emtricitabine.

Human immunodeficiency virus (HIV): A retrovirus that causes immunosuppression in humans (HIV disease) and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

There are two species of HIV that infect humans, namely, HIV-1 and HIV-2. In addition, there are four groups of HIV-1: M, N, O and P, and there are at least nine subtypes and many CRFs of group M: A, B, C, D, F, G, H, J, K and CRFs. Mutant forms of HIV-1 are known that result in the ability of the virus to tolerate antiretroviral treatments (for example the virus can continue to replicate in the presence of the antiretroviral treatments). Such mutants are referred to as HIV-1 drug resistant (HIVDR).

HIV-1 drug resistant (HIVDR): The presence of mutations in HIV-1 (such as one or more amino acid substitutions) that reduce antiviral drug susceptibility (such as susceptibility with antiretroviral therapy or highly active antiretroviral therapy) compared with the susceptibility of wild-type HIV-1. Such strains of HIV-1 can contain one or more mutations in the HIV-1 reverse-transcriptase (RT) or protease (PR) genes. HIVDR can be detected by molecular genotyping, for example using the methods provided herein, by detecting mutations in the RT and/or PR genes.

Mutant forms of HIV include, but are not limited to, those having a mutant reverse transcriptase sequence (e.g., those that have a mutant HIV-1 RT sequence, such as those that are associated with NRTI or NNRTI resistance; see Table 2), and those having a mutant protease sequence (e.g., those that have a mutant HIV-1 PR sequence, such as those that are associated with resistance to protease inhibitors; see Table 1). In particular examples, to detect HIVDR mutations in the RT and protease PR genes genotyping of at least PR codons 10-99 and RT codons 41-240 is performed.

Position numbers for particular HIVDR mutations referred to herein are based on wild-type HIV-1, such as the HXB-2 genome (GenBank Accession number AAC82598).

Exemplary mutant HIV-1 PR sequences include one or more mutations in HIV-PR, such as those listed in Table 1 below. In some examples, the mutant HIV-1 PR sequence that results in drug resistance is a mutation in the protease substrate cleft, such as R8K; R8Q; V82A/T/F/L/T/S; I84V; G48V; D30N, I50V, V32I, M46I, I47V, and I50V; M46I/L, I47V, V82A, and I84V, in the protease flap, such as I54V, I54T/L/M/S, I47V (for example in combination with V32I), F53L, and other regions, such as L90M, G73C/S/T, N88D, N88S, and L24I.

Exemplary mutant HIV-1 RT sequences include one or more mutations in HIV-1 RT, such as those listed in Table 2 below. Particular examples include but are not limited to K20R, T39A, M41L, K43E/Q/N, E44D/A, K65R, D67N, T69D, T69N/S/A, K70R, L74V, V75T, V75I, V75M/A, A98G, L100I, K101E/D/C, K103N, V106A/M, V108I/M, Y115F, V118I, E138K, Q145M, Q151M, P157A/S, V179D, Y181C/I, M184V, Y188L/C/H, G190S/A/E, E203D/K, H208Y, L210W, R211K, L214F, T215Y/F, D218E, H221Y, D223E/Q, P225H, L228H/R, M230L, P236L, K238R/N, Y318F, G333E, N348I or combinations thereof (such as L100I and K103N, K101D and K103N, K103N and Y181C, K103N and V108I, or K103N and K101E/C).

HIV-1 protease (PR): A retroviral aspartyl protease that cleaves newly synthesized polyproteins to create the mature protein components of an infectious HIV virion. HIV-1 protease is responsible for the post-translational processing of the viral Gag and Gag-Pol polyproteins to yield the structural proteins and enzymes of the virus. The HIV-1 protease includes two identical polypeptides of 99 amino acids, each chain having an N-terminal Pro and C-terminal Phe, with an active site from Met-46 to Lys-55. Exemplary protease inhibitors (PIs) include amprenavir, indinavir, lopinavir (manufactured in combination with ritonavir), nelfinavir, ritonavir, saquinavir, atazanavir, tipranavir and TMC114. An exemplary wild-type HIV-PR sequence is provided as amino acids 57 to 155 of GenBank Accession Number AAC82598.

HIV-1 reverse transcriptase (RT): HIV-1 RT is responsible for RNA-dependent DNA polymerization and DNA-dependent DNA polymerization. RT is a heterodimer of p66 and p51 subunits. Exemplary RT inhibitors include NRTIs, such as chain terminators that block further extension of the proviral DNA during reverse transcription (e.g., nucleoside analogs zidovudine, didanosine, zalcitabine, stavudine, lamivudine, abacavir, and emtricitabine, and nucleotide analog tenofovir disoproxil fumarate), and NNRTIs, (e.g., nevirapine, delavirdine, and efavirenz). An exemplary wild-type HIV-RT sequence is provided as amino acids 156 to 848 of GenBank Accession Number AAC82598.

HIV-1 pol gene: The genomic region of HIV-1 that encodes for the viral enzymes protease (PR), integrase (IN) and reverse transcriptase (RT). These enzymes are produced as a Gag-Pol precursor polyprotein, which is processed by the viral protease; the Gag-Pol precursor is produced by ribosome frameshifting near the 3' end of gag. An exemplary HIV pol amino acid sequence is shown in GenBank Accession number AAC82598.

Hybridization: To form base pairs between complementary regions of two strands of DNA, RNA, or between DNA and RNA, thereby forming a duplex molecule. For example, the primers disclosed herein (Table 5) can form a duplex molecule with HIV-1 cDNA (reverse transcribed from HIV-1 RNA), such as an HIV-1 RT or PR sequence. Hybridization conditions resulting in particular degrees of stringency will vary depending upon the nature of the hybridization method and the composition and length of the hybridizing nucleic acid molecules. Generally, the temperature of hybridization and the ionic strength (such as the Na concentration) of the hybridization buffer will determine the stringency of hybridization. However, for hybridization conditions related to PCR, the salt concentration is generally fixed by the buffer conditions and stringency of hybridization controlled by temperature (for example 42° C. low stringency, 48-50° C. medium stringency, and 55-60° C. high stringency).

Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). For purposes of this disclosure, "stringent conditions" encompass conditions under which hybridization only will occur if there is less than 25% mismatch between the hybridization molecule and the target sequence. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Moderately stringent hybridization conditions are when the hybridization is performed at about 42° C. in a hybridization solution containing 25 mM $KPO_4$ (pH 7.4), 5×SSC, 5X Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5X Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 55° C. with a wash solution containing 0.2×SSC and 0.1% sodium dodecyl sulfate.

Very highly stringent hybridization conditions are when the hybridization is performed at about 42° C. in a hybridization solution containing 25 mM $KPO_4$ (pH 7.4), 5×SSC, 5X Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate. 20×SSC is 3.0 M NaCl/0.3 M trisodium citrate.

Isolated: An "isolated" biological component (such as a nucleic acid molecule, for example RNA) has been substantially separated, produced apart from, or purified away from other biological components. Nucleic acid molecules which have been "isolated" include nucleic acids molecules purified by standard purification methods (for example RNA extracted from a clinical sample), as well as those chemically synthesized. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide (such as any of SEQ ID NOS: 1-10), thereby permitting detection of the nucleotide, such as detection of the nucleic acid molecule of which the nucleotide is a part of. Examples of labels include, but are not limited to, radioactive isotopes, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Non-nucleoside reverse transcriptase inhibitor (NNRTI): Non-nucleosides and analogues thereof that significantly reduce or inhibit the activity of HIV reverse transcriptase (e.g., HIV-1 reverse transcriptase), the enzyme which catalyzes the conversion of viral genomic HIV RNA into proviral HIV DNA. Exemplary NNRTIs include but are not limited to nevirapine, delaviradine and efavirenz.

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides.

Nucleoside/nucleotide reverse transcriptase inhibitor (NRTI): Nucleosides, nucleotides, and analogues thereof that significantly reduce or inhibit the activity of HIV reverse transcriptase (e.g., HIV-1 reverse transcriptase). Exemplary NRTIs include but are not limited to zidovudine (AZT), lamivudine (3TC), and zalcitabine (ddC).

Oligonucleotide: A linear polynucleotide (such as DNA or RNA) sequence, for example of at least 6 nucleotides, for example at least 9, at least 15, at least 18, at least 24, at least 30, or at least 50 nucleotides long, such as 12-40 nucleotides, 18 to 35 nucleotides, 18 to 30 nucleotides, 19 to 30 nucleotides, 19 to 29 nucleotides, or 20 to 29 nucleotides. An oligonucleotide can contain non-naturally occurring portions, such as altered sugar moieties or inter-sugar linkages, such as a phosphorothioate oligodeoxynucleotide. In particular examples, an oligonucleotide containing non-naturally occurring portions can bind to RNA or DNA, and include peptide nucleic acid (PNA) molecules. In some examples an oligonucleotide can include unnatural nucleotides.

Primer: A short nucleic acid molecule which can be used to initiate the synthesis of a longer nucleic acid sequence. In one example, a primer includes a detectable label, and is referred to as a probe.

Primers can be annealed to a complementary target DNA strand (such as HIV-1 pol) by nucleic acid hybridization to form a hybrid between the primer and the target DNA strand, and then the primer extended along the target DNA strand by a DNA polymerase enzyme. Primer pairs can be used for amplification of a nucleic acid sequence, for example by PCR or other nucleic-acid amplification methods.

In particular examples, a primer that can be used with the disclosed methods is about 10-50 nucleotides, for example about 12-50 nucleotides, 15-40 nucleotides, 15-30 nucleotides, 12-40 nucleotides, 18 to 35 nucleotides, 18 to 30 nucleotides, 19 to 30 nucleotides, 19 to 29 nucleotides, or 20 to 29 nucleotides.

Reverse transcriptase (RT): An enzyme that can transcribe single-stranded RNA into single-stranded DNA. This enzyme is used by reverse-transcribing RNA viruses, such as HIV-1, to reverse-transcribe their RNA genomes into DNA, which is then integrated into the host genome and replicated along with it. An exemplary reverse transcriptase is a wild-type HIV-1 RT (described above).

Sample: Biological specimens, such as those obtained from a subject that contains nucleic acid molecules (for example DNA, cDNA, RNA, mRNA, or combinations thereof). In one example, a sample is one in which HIV-1 would be found if the subject from which the sample were obtained was infected with HIV-1. In particular examples, a sample is obtained from a subject suspected of suffering from a disease or syndrome that is at least partially caused by HIV-1. The subject may also be an asymptomatic individual considered to be at risk of HIV-1 infection. In a particular example, the sample is obtained from a human subject.

The sample can be a cellular sample such as a blood sample or a portion thereof, such as plasma, serum or peripheral blood mononuclear cells (PBMCs), or a dried form of them (e.g., dried blood, dried PBMC, dried plasma or dried serum), as well as a sample obtained from other bodily tissues or body fluids used in diagnostic testing of HIV.

Sensitivity: The probability that a statistical test will be positive for a true statistic, such as the ability to detect an HIV1DR PR or RT mutation if the mutation is present. Can be calculated by dividing the number of test positive results divided by the number of total test positive and false negative results, and is usually expressed as a percentage.

For example, the sensitivity of the methods disclosed herein is an indication that the methods can detect all known HIV1 group M viral strains. In one example, the sensitivity of the disclosed methods is at least 95%, such as at least 98%, at least 99%, or at least 100%, meaning that at least 95 times out of 100 times the method is performed, the method will detect the presence of HIV1 group M viral strains if present in a sample.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biomedical Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

Once aligned, the number of matches is determined by counting the number of positions where an identical nucleotide is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 19 matches when aligned with a test sequence having 20 nucleotides is 95.0 percent identical to the test sequence (19÷20*100=95.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing 21 nucleotides that aligns with 19 consecutive nucleotides from an identified sequence as follows contains a region that shares 90 percent sequence identity to that identified sequence (that is, 19÷21*100=90).

One indication that two nucleic acid molecules are closely related is that the two molecules hybridize to each other under stringent conditions (such as high or very high stringency), as described above. In some examples, the primers disclosed in SEQ ID NOS: 1-10 can be altered in a few nucleotides (such as 1, 2, 3, 4, or 5 nucleotides) without affecting the ability of the primer to function properly using the methods disclosed herein. In one example, a primer having at least 90% sequence identity, or even at least 95% sequence identity to any of SEQ ID NOS: 1-10, can be used in the methods disclosed herein.

Specificity: The probability that a statistical test will be negative for a negative statistic, such as the ability to not produce a positive result if an HIV-1DR PR or RT mutation is not present. Can be calculated by dividing the number of true negative results by the number total of true negative and false-positive results, and is usually expressed as a percentage.

For example, the specificity of the methods disclosed herein is an indication that the methods cannot amplify a PCR product from a sample which does not contain HIV1 group M viral strains, while not indicating a positive result if the HIV1 group M viral strain is absent (for example if the patient is infected with a hepatitis virus). In one example, the specificity of the disclosed methods is at least 95%, such as at least 98%, at least 99%, or at least 100%, meaning that at least 95 times out of 100 times the method is performed, the method will not detect the presence of HIV1 group M viral strains if they are present in a sample, and not indicate a positive result if such mutations are not present.

Subject: Living multi-cellular vertebrate organisms, a category that includes human and non-human mammals, such as non-human primates. In a particular example, a subject is a human that has or is susceptible to infection with HIV-1.

Under conditions sufficient for: A phrase that is used to describe any environment that permits the desired activity. An example includes contacting primers with a nucleic acid molecule (such as one reverse transcribed from RNA extracted from a sample) with reagents and temperature conditions sufficient to allow amplification of the nucleic acid molecule or sequencing of the nucleic acid molecule.

Overview of the Technology

Even where effective antiretroviral therapy (ART) is available, HIV-1 drug resistance is a crucial issue. For example, numerous individuals who began therapy in the early and mid-1990s already harbor multidrug-resistant viruses. In addition, a significant proportion of new HIV infections that result from the transmission of HIV strains are already resistant to one or more antiretroviral drugs. As the epidemic continues to grow worldwide, increasing numbers of individuals are being treated. The margin of success for achieving and maintaining virus suppression is narrow. Extraordinary patient effort is required to adhere to drug regimens that are expensive, inconvenient, and often associated with dose-limiting side effects. Incomplete virus suppression due to these factors predisposes to the development of drug resistance, which threatens the success of future treatment regimens.

The presence of drug-resistant virus before starting a new drug regimen is an independent predictor of virologic response to that regimen. Several prospective controlled studies have also shown that patients whose physicians have access to drug resistance data, particularly genotypic resistance data, respond better to therapy than control patients whose physicians do not have access to these assays. The accumulation of such retrospective and prospective data has led several expert panels to recommend monitoring virological responses and resistance testing in the treatment of HIV-1-infected patients (such as those receiving ART therapy). Thus, methods are needed that can accurately determine the genotype of HIV-1 in an infected patient, including non-B subtypes of HIV-1.

Commercially available HIV-1 drug resistance (HIVDR) genotyping assays are expensive and fall short in detecting non-B subtypes and circulating recombinant forms that are co-circulating in resource-limited settings. Herein provided are methods that optimize a broadly sensitive in-house assay in detecting HIVDR mutations in protease (PR) and reverse transcriptase (RT) regions of HIV-1 pol gene. The overall genotyping sensitivity was 95.8% (92/96). Compared to the original in-house assay and two commercially available genotyping systems, TRUGENE and ViroSeq, the optimized in-house assay showed a nucleotide sequence concordance of 99.3%, 99.6% and 99.1%, respectively. The optimized in-house assay was more sensitive in detecting nucleotide mixtures than the original in-house (n=87, P<0.001) and TRUGENE and ViroSeq assays. When the optimized in-house assay was applied to a transmitted HIVDR survey in Vietnam, all 72 (100%) plasma and 69 of 72 (95.8%) matched DBS were genotyped, and sequences between plasma and the DBS were 98.8% concordant. All 46 samples from ART-experienced patients from Malawi and Nigeria with VL≥3 log 10 and 78.6% (11/14) of plasma samples with VL<3 log 10 copies/ml were genotyped by the assay. Furthermore, all 18 matched DBS stored at room temperature for an average of 85 days from Nigerian ART-patients with plasma VL≥3 log 10 copies/ml were genotyped. Phylogenetic analysis of the 236 sequences revealed that 43.6% were CRF01_AE, 25.9% subtype C, 13.1% CRF02_AG, 5.1% subtype G, 4.2% subtype B, 2.5% subtype A, 2.1% each subtype F and unclassifiable (UC), 0.4% each CRF06_CPX, CRF07_BC and CRF09_CPX.

Plasma is currently the gold standard for HIV-1 viral load (VL) and HIVDR genotyping and is the only recommended specimen type for VL and HIVDR genotyping of patients on ART for monitoring surveys [23]. This makes implementing monitoring surveys in resource-limited settings difficult as plasma requires immediate processing and cold-chain storage and transportation. It is also shown herein that dried blood spots (DBS) can be used for VL measurements and HIVDR genotyping, for example in resource-limited settings. Direct comparison of VL levels showed that DBS, and not DPS, gave comparable results to plasma (P=0.0619 and 0.0007, respectively) using commercially available VL kit; however both DBS and DPS had excellent correlation with plasma in predicting virological failure (VL≥1,000 copies/ml) in patients (Kappa=0.78 and 0.83, respectively). Of the 18 specimens with a plasma VL≥1,000 copies/ml, HIVDR genotyping rates were 100% in DBS and 38.9% in DPS, and DBS identified 61 (93.8%) out of 65 HIVDR mutations identified in plasma specimens.

Based on these results, the disclosure provides methods that are broadly sensitive in genotyping HIV-1 group M viral strains and more sensitive than the original in-house, TRU-GENE and ViroSeq in detecting mixed viral populations. The broad sensitivity and substantial reagent cost saving make this assay more accessible for resource-poor settings where HIVDR surveillance and monitoring are recommended to prevent the development and transmission of HIVDR.

It is shown herein that the methods are broadly sensitive in genotyping multiple HIV-1 group M viruses and CRFs from plasma and dried blood spots (DBS) collected from six resource-limited countries. A previous assay, although a success from the broad sensitivity perspective, was in need of improvement due to the concern of incomplete genotyping of the HIV protease (PR) gene and suboptimal sequence quality due to primer design [22]. The validation of the re-designed RT-PCR assay and the sequencing primers in the current disclosure confirmed that the newly optimized assay is comparable to the original assay in assay sensitivity and specificity and it is also broadly sensitive to all group M subtypes and CRFs circulating in several PEPFAR-supported countries. Pairwise nucleotide sequence identity analysis from sequences generated by the disclosed assay and the sequences obtained from the original assay and two commercially available genotyping systems indicated the disclosed assay produced comparable genotyping results. In addition, the disclosed assay expanded genotyping codon coverage to include all PR mutations and improved sequence quality by reducing background noises to minimal, resulting in more sensitive mixture calling The ability to detect nucleotide mixtures (low frequency viral strains) is important as recent studies have demonstrated that low frequency variants can grow rapidly and become predominant viral population under the selection pressure and lead to treatment failure [31,32].

The disclosed assay was highly sensitive in genotyping B and non-B subtype viral strains of HIV-1 group M viruses. In addition, the assay efficiently genotyped plasma and DBS samples from various geographical areas. The disclosed assay was able to genotype 100% of plasma samples collected from virological failure patients, defined as VL≥3 log 10 copies/ml [4] herein and over two thirds of patients with VL between 2.18 and ≤3 log 10 copies/ml. Genotyping was successful for all 18 matched DBS samples collected from Nigerian patients with virological failure. It is noted that these DBS samples had been stored at room temperature for an average of 85 days before shipping to the laboratory for testing. In addition, testing of two DBS PT panels shipped frozen or at ambient temperature revealed that genotyping was successful for all DBS samples except one with the lowest VL level and shipped at ambient temperature. These results demonstrate that the disclosed method is highly sensitive in genotyping both plasma and DBS samples even when the DBS samples were stored at suboptimal conditions for long periods of time (for example for more than 60 days).

Comparing the performance of the disclosed assay with TRUGENE, ViroSeq and the original assay, high nucleotide sequence identity was revealed; however, minor differences existed in mixture base callings. The disclosed assay detected more mixture bases than the commercial kits and the original in-house assay. Many factors could contribute to the sequence discordances at the nucleotide mixture sites in HIV genotyping including viral quasispecies, primer binding preference and location, Taq polymerase misincorporation, sequence quality, base-calling criteria or technical errors [11,33,34]. Because HIV-1 viruses are rapidly evolving quasispecies [35], there are multiple HIV-1 variants in one patient [33,36]. Sequence identity and codon concordance are challenging when mixtures are present [37]. It has been reported that ViroSeq detected more mixtures (78%) than an in-house assay (22%) [10]. In contrast, the disclosed assay detected more mixture bases than other assays. This may be due to the fact that the disclosed assay produced sequence chromatographs containing minimal background noise. To confirm this, sequence editing was performed for all validation samples (n=102) including PT panels with ReCall program [26] using default mixture calling minor peak setting at >15% of the major peak in bi-directional sequences. In addition, one set of the PT panels was tested by three different operators. These analyses showed that the disclosed assay gave more sensitive mixture calling. The variability in detecting nucleotide mixtures was likely due to the first-round RT-PCR [38] and in sampling of the HIV-1 quasispecies by PCR rather than by technical errors in the sequencing process [39]. The use of wide-spectrum degenerate primers and a mixture of two forward primers at slightly different binding sites in the initial run of PCR likely contributed to more mixtures calling in the disclosed assay.

Phylogenetic analysis indicated that the disclosed assay could genotype subtypes A (A1, A2), B, C, D, F (F1, F2), G, H, K, and CRFs including CRF01_AE, CRF02_AG, CRF06_CPX, CRF07_BC, CRF09_CPX and UC with an overall sensitivity of 96% using specimens from different geographical regions around the world. It has been reported that genotyping sensitivity with two FDA-approved systems using non-B subtypes varies [40]. Some studies indicated that these two systems performed well for subtypes B and non-B [9,41,42,43] while others demonstrated that they were less sensitive to non-B subtypes and CRFs [12,13,14, 44]. For instance, only 52% of serum samples were genotyped in an Ethiopian threshold survey using ViroSeq and TRUGENE methods sequentially [45]. For genotyping DBS samples collected from subtype B infected persons, one study reported 78.8% genotyping rate by TRUGENE [46] while a second study reported 57.5% DBS samples stored for one year at 4° C. were genotyped using ViroSeq [47]. Another study reported an even lower DBS genotyping rate of 38.6% by ViroSeq system. Compared to these commercial assays, the disclosed assay was not only sensitive, but also inexpensive. The assay could reduce the cost for genotyping reagents by 75%.

Methods of HIV-1 Genotyping

The present disclosure provides methods for genotyping HIV-1, for example HIV-1 present in a sample obtained from a subject. As disclosed herein, such methods can be used to determine if the subject is infected with HIV, for example to determine if the subject is infected with an HIVDR mutation present in HIV pol (such as a mutation in an HIV protease protein or reverse transcriptase protein that results in drug resistance). Such methods can be used for surveillance of HIV-1 drug resistance and monitoring patients on antiretroviral therapy. In contrast to previous methods, which focus on detection of HIV subtype B, the disclosed methods permit genotyping HIV-1 of group M subtypes, such as B as well as non-B subtypes A, C, D, F, G, H, J and K, as well as CFRs and unique recombinant forms (URFs).

In particular examples, the methods have a specificity of at least 99%, such as at least 99.5%, or at least 99.9%. In particular examples, the methods have a sensitivity of at least 95%, such as at least 96%, such as at least 97%, at least 98% or at least 99%.

The disclosed methods can include contacting a sample obtained from a subject with a first forward nucleic acid primer (also referred to herein as a degenerate oligonucleotide or primer) comprising or consisting of SEQ ID NO: 1 and 2 or comprising or consisting of SEQ ID NO: 3, and a first reverse nucleic acid primer comprising SEQ ID NO: 4, thereby generating a first reaction mixture. The first reaction mixture is incubated under conditions sufficient to amplify a portion of HIV-1 pol in the first reaction mixture thereby generating a first amplification product. In some examples, the first reaction mixture is incubated under conditions sufficient to amplify a portion of HIV-1 pol in the first reaction mixture using reverse transcription polymerase chain reaction (RT-PCR), thereby generating an RT-PCR product. In some examples, for example when the viral load is high, the first amplification product is sequenced or subjected to allele-specific techniques to detect HIVDR mutations present in the first amplification product. In some examples, the sequencing of the first amplification product includes contacting the first amplification product with nucleic acid primers comprising or consisting of SEQ ID NOS: 5-10.

In some examples, for example if the first amplification product is not sequenced or subjected to allele-specific techniques (for example when the viral load is low), the resulting first amplification product (or RT-PCR product) can be contacted with a second forward nucleic acid primer comprising or consisting of SEQ ID NO: 5 and a second reverse nucleic acid primer comprising or consisting of SEQ ID NO: 6, thereby generating a second reaction mixture. The second reaction mixture is incubated under conditions sufficient to amplify the region of HIV-1 pol encompassing PR and RT in the second reaction mixture, thereby generating a second amplification product. In some examples, the second reaction mixture is incubated under conditions sufficient to amplify the region of HIV-1 pol encompassing PR and RT in the second reaction mixture using nested PCR, thereby generating a nested PCR product. The second amplification product (or nested PCR product) can then be sequenced, wherein sequencing determines the genotype of HIV-1. In some examples, the sequencing of the second amplification product (or nested PCR product) includes contacting the second amplification product (or nested PCR product) with nucleic acid primers comprising or consisting of SEQ ID NOS: 5-10.

One skilled in the art will appreciate that minor changes can be made to any of the disclosed primers, and the variant primers used in the methods provided herein, such as a primer having at least 90%, at least 95%, at least 97%, at least 98%, at least 99% or 100% sequence identity to SEQ ID NO: 1, 2, 3, 5, 7, 8, 9 or 10 that is 18 to 35 nucleotides in length.

In some examples, HIV-1 is genotyped using HIV-1 DNA obtained from peripheral blood mononuclear cells (PBMC). In such examples, only a single amplification reaction is needed (e.g., no RT-PCR is needed). For example, the HIV-1 DNA can be incubated with a forward nucleic acid primer comprising or consisting of SEQ ID NO: 1, 2, 3, or 5 and a reverse nucleic acid primer comprising or consisting of SEQ ID NO: 4 or 6, thereby generating a reaction mixture. The reaction mixture is incubated under conditions sufficient to amplify a portion of HIV-1 pol that includes HIV-1 reverse transcriptase (RT) and HIV-1 protease (PR), thereby generating an amplification product. The resulting amplification product is sequenced to determine the genotype of HIV-11 or HIVDR mutations can be detected with allele-specific techniques.

In some examples, the method can further include comparing the sequence of the first amplification product (or RT-PCR product) and/or second amplification product (or nested PCR product) (such as the PR or RT amino acid sequence) to the WHO surveillance drug resistance mutation (SDRM) list or International AIDS Society (IAS) HIV drug resistance mutation list. Such methods can be used for population-based surveillance and monitoring of drug resistance (DR) in resource-limited settings. Identifying the pattern and rates of transmitted and acquired HIVDR variants can be used to collectively inform regional and global recommendations on which ARVs to maintain or change in first and second-line regimens. Furthermore the disclosed methods can permit detection of a new drug resistant HIV-1 mutation, such as those not currently found on the WHO SDRM or IAS HIV drug resistance mutation list. Upon the identification of a new drug resistant HIV-1 mutation, such a mutation can be added to the WHO SDRM or IAS HIV drug resistance mutation list (thereby revising the SDRM or IAS HIV drug resistance mutation list).

In some examples, the methods can also include obtaining nucleic acid molecules from the sample, prior to genotyping HIV-1, for example isolating RNA from the sample prior to contacting the sample with the first and second nucleic acid primers. In some examples, DNA is isolated from the sample (such as a sample that includes PBMCs) prior to contacting the sample with the amplification primers. In some examples, the amplification product (such as the first amplification product (or RT-PCR product) and/or second amplification product or nested PCR product) is purified or isolated prior to sequencing. For example, the resulting amplification reaction (such as the first amplification product (or RT-PCR product) and/or the nested PCR amplicons) can be subjected to agarose gel electrophoresis, and the amplicons of the correct length (e.g., about 1,084 nucleotides) isolated and used for sequencing. Other methods of isolating amplicons from a PCR reaction mixture can be used, such a purification using a silicon column, gel filtration, or precipitation with salt solution.

In some embodiments, once a patient's HIV-1 genotype is determined, an indication of that genotype can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

In other examples, the output is a graphical representation, for example, a graph that indicates the sequence of the patient's HIV-1 genotype, for example in comparison to a wild-type HIV-1 sequence. In some examples, the output is communicated to the user, for example by providing an output via physical, audible, or electronic means (for example by mail, telephone, facsimile transmission, email, or communication to an electronic medical record).

In some examples, the output can provide a recommended therapeutic regimen. For example if a particular HIVDR mutation is present (or absent), a particular therapy can be recommended. In some examples, the test may include determination of other clinical information, such as determining the amount of HIV-1 present in the sample, for example determining an HIV-1 viral load in the subject. Such methods are routine in the art.

In some embodiments, the disclosed methods of HIV-1 genotyping include one or more of the following depending on the patient's HIV-1 genotype: a) prescribing a treatment regimen for the patient if the patient's determined HIV-1 genotype is considered to be negative for a HIVDR mutations; b) prescribing a treatment regimen for the patient if the patient's determined HIV-1 genotype is considered to be positive for an HIV-1 PR mutation associated with drug resistance; c) prescribing a treatment regimen for the patient if the patient's determined HIV-1 genotype is considered to be positive for an HIV-1 RT mutation associated with drug resistance; d) prescribing a treatment regimen for the patient if the patient's determined HIV-1 genotype is considered to be positive for an HIV-1 PR and an HIV-1 RT mutation associated with drug resistance; e) administering a treatment to the patient based on the prescriptions of a)-d) if the patient's determined HIV-1 genotype is one that will respond a particular drug therapy; and f) not administering a treatment regimen to the patient if the patient's determined HIV-1 genotype is considered to be one that will result in resistance to known therapies for HIV-1. In an alternative embodiment, the method can include recommending one or more of a)-f).

Methods of Nucleic Acid Amplification

Methods of amplifying a nucleic acid molecule, such as HIV pol (for example a region including HIV PR or RT associated with HIVDR), are well known in the art. The disclosure is not limited to particular amplification methods.

Briefly, a representative process starts with isolating RNA (such as viral RNA) from the sample obtained from the patient. Protein and DNA can be removed. If desired, the RNA concentration can be determined. RNA repair and/or amplification steps can be included. The HIV-1 pol RNA in the isolated RNA (if present) is reverse transcribed into cDNA, for example using the primers provided herein and RT-PCR.

Generally, the first step in gene expression profiling by RT-PCR is the reverse transcription of the RNA template into cDNA, followed by its exponential amplification in a PCR reaction. The reverse transcription step is typically primed using specific primers. For example, extracted RNA can be reverse-transcribed using a SuperScript™ III one step RT/Platinum® Taq high Fidelity Enzyme Mix (Invitrogen, Carlsbad, Calif.), following the manufacturer's instructions. Although the PCR step can use a variety of thermostable DNA-dependent DNA polymerases, it typically employs the Taq DNA polymerase.

The derived cDNA can then be used as a template in the subsequent PCR reaction. For example, the resulting cDNA can be amplified using PCR (such as nested PCR). Nested PCR can be used to reduce the contamination in amplification products due to the amplification of unexpected primer binding sites. By using RT-PCR followed by nested PCR, the first PCR reaction produces a larger fragment of HIV-1 pol 1313 nucleotides (nt), while the nested PCR reaction amplifies a target that includes HIV RT and PR of 1068 nt within the first amplicon generated A variation of RT-PCR is real time quantitative RT-PCR, which measures PCR product accumulation through a dual-labeled fluorogenic probe (e.g., Taqman® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, Calif.).

TaqMan® RT-PCR can be performed using commercially available equipment, such as, for example, ABI PRISM 7700® Sequence Detection System® (Perkin-Elmer-Applied Biosystems, Foster City, Calif.), or Lightcycler® (Roche Molecular Biochemicals, Mannheim, Germany). In one example, the 5' nuclease procedure is run on a real-time quantitative PCR device such as the ABI PRISM 7700® Sequence Detection System®. In some examples, 5'-nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

In another example, a representative process starts with isolating DNA (such as viral DNA) from the sample obtained from the patient. Protein and RNA can be removed. If desired, the DNA concentration can be determined. DNA repair and/or amplification steps can be included. The HIV-1 pol DNA in the isolated DNA (if present) can be amplified to permit its sequencing, for example using the primers provided herein and PCR (such as nested PCR). Such a PCR reaction amplifies a target that includes HIV RT and PR (1068 nt) within the amplicon generated.

To minimize errors and the effect of sample-to-sample variation, RT-PCR or other PCR reaction can be performed using an internal standard. An exemplary internal standard is expressed at a constant level among different tissues, and is unaffected by an experimental treatment. RNAs or DNAs commonly used to normalize patterns of gene expression are mRNAs or cDNAs for the housekeeping genes GAPDH, β-actin, and 18S ribosomal RNA.

Methods of Sequencing or Detecting Specific Alleles

Methods of sequencing a nucleic acid molecule, such as a PCR amplicon, are well known in the art. Similarly, methods of detecting a mutation using allele-specific techniques are well known in the art. The disclosure is not limited to particular sequencing or allele-specific detection methods.

HIVDR Mutations

Mutations in the HIV-1 protease (PR) and reverse transcriptase (RT) proteins are associated with HIV drug resistance (HIVDR), such as resistance to NNRTIs, NRTIs, and protease inhibitors. Thus, in one example genotyping HIV-1 permits detection of one or more HIV-1 PR or RT mutations known to be associated with drug resistance, or are newly identified as causing HIV-1 drug resistance.

In one example, the HIV-1 genotype detected is a mutation in an HIV PR protein. For example, mutations at positions shown in column 1 of Table 1 are known to be associated with HIVDR. In specific examples, the methods detect one or more of the following HIV PR mutations shown in Table 1, such as L10I, L23I, V32A, L33F, E35G, M46L, I54V, A71V, A71T, T74S, V82A, N88G, L90M, or combinations thereof. Position numbers for particular HIVDR mutations referred to herein are based on wild-type HIV-1, such as the HXB-2 genome (GenBank Accession number AAC82598).

TABLE 1

HIVDR mutations in HIV protease

| HIV-1 amino acid position | Amino acid substituted |
|---|---|
| 54 | V |
| 48 | V |
| 82 | T |
| 30 | N |
| 54 | L |
| 76 | V |
| 71 | I |
| 54 | M |
| 82 | F |
| 82 | S |
| 54 | A |
| 50 | V |
| 50 | L |
| 54 | S |
| 47 | A |
| 84 | V |
| 20 | T |
| 32 | I |
| 54 | T |
| 82 | A |
| 73 | S |
| 24 | I |
| 53 | L |
| 88 | D |
| 88 | S |
| 47 | V |
| 10 | F |
| 90 | M |
| 46 | L |
| 58 | E |
| 46 | I |
| 33 | F |
| 20 | M |
| 71 | V |
| 71 | T |
| 10 | I |
| 10 | V |
| 20 | R |
| 20 | I |
| 36 | I |
| 73 | T |
| 82 | M |
| 10 | R |
| 73 | A |
| 71 | L |
| 84 | A |
| 53 | Y |
| 85 | V |
| 74 | P |
| 82 | L |
| 89 | V |
| 43 | T |
| 35 | G |
| 20 | V |
| 33 | I |
| 11 | I |
| 36 | L |
| 36 | V |
| 33 | V |
| 16 | E |
| 77 | I |
| 63 | P |
| 82 | I |
| 69 | K |
| 48 | M |
| 82 | C |
| 83 | D |
| 89 | T |
| 23 | I |
| 73 | C |
| 93 | M |
| 89 | I |
| 74 | S |
| 60 | E |
| 62 | V |
| 64 | V |
| 93 | L |
| 89 | M |
| 13 | V |
| 95 | F |
| 88 | G |
| 10 | Y |
| 48 | A |
| 84 | C |
| 45 | I |
| 24 | F |
| 41 | T |
| 70 | E |
| 34 | Q |
| 16 | A |
| 64 | M |
| 69 | Y |
| 15 | V |
| 35 | D |
| 41 | K |
| 74 | E |
| 32 | L |
| 48 | T |
| 46 | F |
| 10 | C |
| 88 | T |
| 33 | M |
| 53 | W |
| 36 | A |
| 32 | ins |
| 48 | S |
| 97 | V |
| 77 | V |
| 89 | R |
| 82 | G |
| 73 | F |
| 71 | F |
| 15 | A |
| 57 | R |
| 11 | V |
| 8 | K |
| 91 | S |
| 11 | L |
| 4 | P |
| 46 | V |
| 38 | W |
| 77 | T |
| 66 | F |
| 11 | F |
| 8 | Q |
| 32 | A |
| 11 | C |
| 73 | V |
| 34 | V |
| 69 | I |
| 77 | A |
| 65 | Q |
| 20 | L |
| 11 | T |
| 41 | I |
| 10 | M |
| 22 | V |
| 55 | R |
| 69 | N |
| 92 | K |
| 36 | T |
| 74 | A |
| 35 | N |
| 61 | H |
| 69 | R |
| 12 | K |
| 43 | R |
| 63 | Q |
| 64 | L |
| 63 | A |
| 63 | S |
| 69 | Q |

TABLE 1-continued

HIVDR mutations in HIV protease

| HIV-1 amino acid position | Amino acid substituted |
|---|---|
| 63 | C |
| 45 | R |
| 37 | D |
| 63 | T |
| 70 | R |
| 14 | R |
| 57 | K |

In one example, the HIV-1 genotype detected is a mutation in an HIV RT protein. For example, mutations at the positions listed in the left-hand column of Table 2 are known to be associated with HIVDR. In specific examples, the methods detect one or more of the following HIV-1 RT mutations shown in Table 2, such as M41L, A62V, K65R, D67N, T69S/N, V90I, A98G, K101E/Q, K103N, V106A/I, V118I, E138A, V179D/T, Y181C, M184V, Y188C/L, G190A, L210F, T215A, H221Y, or combinations thereof. Position numbers for particular HIVDR mutations referred to herein are based on wild-type HIV-1, such as the HXB-2 genome (GenBank Accession number AAC82598). In one example, the method permits detection of an HIV-1 RT mutation at amino acid positions 1 to 251.

TABLE 2

HIVDR mutations in HIV reverse transcriptase

| HIV-1 amino acid position | Amino acid substituted |
|---|---|
| 67 | N |
| 210 | W |
| 106 | M |
| 219 | E |
| 225 | H |
| 100 | I |
| 151 | M |
| 70 | E |
| 190 | S |
| 115 | F |
| 101 | P |
| 69 | ins |
| 181 | V |
| 179 | F |
| 215 | F |
| 181 | C |
| 106 | A |
| 188 | C |
| 181 | I |
| 215 | Y |
| 65 | R |
| 103 | N |
| 70 | R |
| 190 | A |
| 74 | V |
| 101 | E |
| 188 | L |
| 184 | I |
| 188 | H |
| 219 | Q |
| 98 | G |
| 184 | V |
| 41 | L |
| 179 | D |
| 106 | I |
| 44 | A |
| 75 | T |
| 190 | C |
| 190 | Q |
| 190 | T |
| 69 | D |
| 74 | I |

TABLE 2-continued

HIVDR mutations in HIV reverse transcriptase

| HIV-1 amino acid position | Amino acid substituted |
|---|---|
| 103 | T |
| 103 | S |
| 190 | E |
| 67 | G |
| 219 | R |
| 190 | V |
| 219 | N |
| 69 | N |
| 75 | M |
| 69 | A |
| 44 | D |
| 108 | I |
| 230 | L |
| 75 | S |
| 215 | V |
| 67 | del |
| 103 | H |
| 227 | C |
| 238 | T |
| 116 | Y |
| 215 | E |
| 67 | E |
| 69 | G |
| 215 | I |
| 215 | C |
| 138 | K |
| 75 | A |
| 77 | L |
| 215 | S |
| 215 | D |
| 236 | L |
| 69 | S |
| 101 | Q |
| 227 | L |
| 75 | I |
| 103 | R |
| 118 | I |
| 179 | E |
| 62 | V |
| 67 | S |
| 70 | S |
| 219 | W |
| 70 | G |
| 215 | H |
| 215 | G |
| 101 | N |
| 234 | I |
| 215 | N |
| 215 | L |
| 65 | N |
| 103 | E |
| 103 | Q |
| 215 | A |
| 75 | L |
| 101 | R |
| 90 | I |
| 179 | I |
| 98 | S |
| 101 | H |
| 219 | H |
| 238 | S |
| 69 | E |
| 67 | T |
| 67 | H |
| 119 | S |
| 151 | L |
| 69 | del |
| 181 | S |
| 68 | Y |
| 227 | Y |
| 214 | F |
| 68 | ins |
| 233 | E |
| 215 | Z |
| 145 | M |
| 156 | A |

TABLE 2-continued

HIVDR mutations in HIV reverse transcriptase

| HIV-1 amino acid position | Amino acid substituted |
|---|---|
| 112 | S |
| 161 | L |
| 52 | R |
| 179 | M |
| 70 | N |
| 219 | T |
| 188 | F |
| 89 | G |
| 92 | I |
| 89 | K |
| 100 | V |
| 157 | S |
| 54 | D |
| 101 | I |
| 62 | T |
| 88 | G |
| 184 | T |
| 208 | Y |
| 106 | L |
| 190 | R |
| 165 | A |
| 67 | A |
| 179 | A |
| 70 | T |
| 227 | S |
| 143 | S |
| 145 | L |
| 221 | Y |
| 218 | E |
| 210 | S |
| 88 | S |
| 179 | G |
| 141 | E |
| 238 | N |
| 139 | I |
| 203 | K |
| 43 | Q |
| 210 | F |
| 210 | M |
| 68 | N |
| 69 | I |
| 236 | S |
| 135 | M |
| 179 | T |
| 50 | V |
| 189 | I |
| 138 | A |
| 68 | G |
| 196 | E |
| 83 | K |
| 35 | I |
| 123 | G |
| 39 | A |
| 135 | L |
| 135 | T |
| 43 | E |
| 238 | R |
| 211 | K |
| 122 | E |

Therapy Selection

In some examples, the methods can be used to select a therapy for a patient infected with HIV-1. For example, if a patient is identified as not having an HIVDR mutation, then the patient can be treated with traditional AVTs, such as NNRTIs, NRTIs, and/or protease inhibitors (or whatever AVT is available). In a specific example, if a patient is identified as not having an HIVDR mutation, then the patient can be selected and treated with HAART.

In contrast, if a patient is identified as having one or more HIVDR mutations, the patient is identified as one who will not benefit from particular ARTs. Mutations associated with particular resistance to a particular drug are known. Thus, if the subject is found to have an HIVDR associated with resistance to a particular drug, the patient should not be treated with that drug as their HIV-1 will be resistant and not treatable with that drug. A different therapy should be selected.

For example, if the patient is found to have one or more HIVDR mutations in the PR protein (such as one or more of the mutations listed in Table 1), the patient should not be treated with a protease inhibitor, such as amprenavir, indinavir, lopinavir, nelfinavir, ritonavir, saquinavir, or atazanavir (or at least not treated with the PR inhibitor associated with their HIVDR mutation). For example, a patient having the HIVDR PR mutation V82A/T/F/S should not be treated with indinavir or ritonavir, while a patient having the HIVDR PR mutation D30N should not be treated with nelfinavir. Instead, such patients could be treated with a RT inhibitor, such has an NNRTI or NRTI. Alternatively, such patients could be treated with other PR inhibitors; for example a patient having the HIVDR PR mutation D30N could be treated with lopinavir or ritonavir.

In contrast, if the subject is determined to have one or more HIV-1 RT mutations (such as one or more of the mutations listed in Table 2), then the patient will not benefit from RT inhibitor therapy and should not be treated with an RT inhibitor (or at least not treated with the RT inhibitor associated with their HIVDR mutation). For example, a patient having the HIVDR RT mutation K70R should not be treated with the NRTI zidovudine, while a patient having the HIVDR RT mutation K103N should not be treated with any NNRTI. Instead, such patients can be treated with protease inhibitors (such as one or more of amprenavir, indinavir, lopinavir, nelfinavir, ritonavir, saquinavir, and atazanavir). Alternatively, such patients could be treated with other RT inhibitors; for example a patient having the HIVDR RT mutation K103N could be treated with an NRTI.

If the patient is determined to have a combination of HIV-1 PR and RT mutations, then the patient will not benefit from protease inhibitor or RT inhibitor therapy (such as one that they are currently on). Instead, patients with one or more HIVDR mutations in both RT and PR can be treated with those ARVs for which are not associated with resistance due to the HIVDR mutation that patient has. For example a patient having the HIVDR PR mutation V32I the HIVDR RT mutation L74V could be treated with a nelfinavir and an NNRTI.

Subjects

The disclosed methods can be used to genotype HIV-1 in a mammalian subject, such as a human subject. In particular examples, the subject is one that lives or has lived in Africa, Latin America, or Asia, or other area where HIV-1 group M is prevalent (e.g., where group M non-subtype B is prevalent). In some examples, the subject is of African (such as from sub-Saharan Africa, for example Cameroon, Nigeria, Malawi, Zambia, Kenya, or Tanzania), Latin American, or Asian (such as from Vietnam, Cambodia, Japan, China, or Thailand) descent.

In particular examples, the methods include selecting a subject that is known to be infected with, or suspected of being infected with, HIV-1. Therefore, in some examples, the subject is one who is known or suspected of being infected with HIV-1, such as HIVDR. In some examples, the subject is at risk for HIV-1 infection, for example medical personnel, prostitutes, or people living in countries where HIV-1 (particularly HIV-1 group M, such as group M non-subtype B) is prevalent (such as Africa, for example, Kenya, Tanzania, Uganda, South Africa, Cameroon, Zambia; or Asia, such as Indonesia, Thailand, Cambodia, or Vietnam). In some examples, the subject is known to be infected with HIV-1. In some examples, the subject to be tested has an HIV viral load of no more than 3 log 10 copies/ml, no more than 2.5 log 10 copies/ml, or no more than 2 log 10 copies/ml. In some examples, the subject to be tested has an HIV viral load of at least 2 log 10 copies/ml, at least 3 log 10 copies/ml, at least 5 log 10 copies/ml, or at least 8 log 10 copies/ml. In some examples, the subject to be tested has an HIV viral load of 3 to 10 log 10 copies/ml, such as 3 to 5 log 10 copies/ml, 3 to 4 log 10 copies/ml, 3 to 6 log 10 copies/ml, or 3 to 8 log 10 copies/ml. In one example, the subject to be tested has a detectable viral load.

In some examples, the methods can include selecting a subject that is known to be infected with, or suspected of being infected with a strain of HIV-1 that is drug resistant. Therefore, in some examples, the subject is one who is known or suspected of being infected with a strain of HIV-1 that is drug resistant. For example, the subject can be one who has been previously treated with one or more antiretroviral therapies (ARTs) (such as anti-retroviral drugs (ARVs)), and for example is no longer responding to the therapy.

In one example, the subject has been previously treated with one or more antiretroviral therapies (ARTs). In another example, the subject is ART-naïve.

Samples

Samples used with the disclosed methods are conventional. For example, the sample can be blood sample or fraction thereof, such as plasma, PBMCs, or a dried version thereof, such as a dried blood spot (DBS). In some examples, the sample is stored prior to analysis, for example, stored at ambient temperature for at least 24 hours, at least 7 days, at least 30 days, at least 60 days, at least 90 days, or at least 120 days, or at least one year, such as 24 hours to 120 days, 7 days to 90 days, or 30 to 90 days. In another example, the sample is stored frozen (e.g., about −20° C. or −80° C.) for at least 24 hours, at least 7 days, at least 30 days, at least 60 days, at least 90 days, or at least 120 days, or at least one year, such as 24 hours to 120 days, 7 days to 90 days, or 30 to 90 days. In some examples, the sample is used directly (e.g., within less than 4 hours).

The sample can be treated prior to performing the methods, for example, concentrated, fractionated, purified or dried. In some examples, nucleic acid molecules are purified or retrieved from the sample prior to analysis. For example, total RNA from samples can be isolated using routine methods. In another example, DNA (such as cDNA) from samples can be isolated using routine methods.

Nucleic acids (such as mRNA or cDNA) can be isolated from the sample according to any of a number of methods well known to those of skill in the art. Methods of isolating total mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993).

In one example, the total nucleic acid is isolated from a sample using, for example, an acid guanidinium-phenol-chloroform extraction method, and polyA+mRNA is isolated by oligo dT column chromatography or by using (dT) magnetic beads (see, for example, Sambrook et al, *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, N.Y. (1987)). In another example, oligo-dT magnetic beads may be used to purify mRNA (Dynal Biotech Inc., Brown Deer, Wis.). General methods for mRNA extraction are well known in the art and are disclosed in standard textbooks of molecular biology, including Ausubel et al., *Current Protocols of Molecular Biology*, John Wiley and Sons (1997).

In another example, RNA isolation can be performed using purification kit, buffer set and protease from commercial manufacturers, such as QIAGEN® (Valencia, Calif.), according to the manufacturer's instructions. For example, total RNA from cells (such as those obtained from a subject) can be isolated using QIAGEN® RNeasy mini-columns. Other commercially available nucleic acid isolation kits include MASTERPURE® Complete DNA and RNA Purification Kit (EPICENTRE® Madison, Wis.), and Paraffin Block RNA Isolation Kit (Ambion, Inc.). Total RNA from samples can be isolated using RNA Stat-60 (Tel-Test). RNA prepared from a sample can be isolated, for example, by cesium chloride density gradient centrifugation.

Isolated Nucleic Acid Molecules

The present disclosure provides isolated nucleic acid molecules, such as primers, which can be used to practice the methods disclosed herein. In some examples such primers are referred to as degenerate oligonucleotides. However, one skilled in the art will appreciate that a few nucleotide substitutions can be made, without affecting the ability of the primer to function properly (e.g., can still amplify or sequence an HIV pol sequence).

Thus, the disclosure provides an isolated nucleic acid molecule (or degenerate oligonucleotide) consisting of the sequence shown in any of SEQ ID NOS: 1-10, such as the sequence shown in SEQ ID NO: 1, 2, 3, 4, 5, 6, 7, 8, 9 or 10. For example SEQ ID NOS: 1 and 2 can be used as forward primers, in combination with SEQ ID NO: 4, to RT-PCR cDNA from mRNA isolated from a sample. If no product is obtained, SEQ ID NO: 3 can be used as a forward primer, in combination with SEQ ID NO: 4 to RT-PCR cDNA from mRNA isolated from a sample. SEQ ID NO: 5 can be used as a forward primer, in combination with the reverse primer shown in SEQ ID NO: 6, in a nested PCR reaction to amplify the RT-PCR product. Alternatively, SEQ ID NO: 5 (or SEQ ID NO: 1 or 2) can be used as a forward primer, in combination with the reverse primer shown in SEQ ID NO: 6 (or SEQ ID NO: 4), in a PCR reaction to amplify HIV-1 DNA obtained directly from a sample (such as PBMCs). The resulting amplicon can be sequenced using SEQ ID NOS: 5-10.

Although particular examples of primers are provided, one skilled in the art will appreciate that small changes (such as nucleotide substitutions, deletions, additions, or combinations thereof) can be made to the disclosed primers, particularly in the 5'-end but less so at the 3'-end. For example, up until the final three to five nucleotides of the disclosed primers (that is, the final three to five nucleotides on the 3'-end), a few nucleotide changes can be made, for example nucleotide substitutions, deletions, additions, or combinations thereof, that result in a sequence having at least 90%, at least 95%, at least 97% or at least 98% sequence identity to any of SEQ ID NOS: 1-10. Thus, provided are isolated nucleic acid sequences (or degenerate primers) that have at least 90%, at least 95%, at least 97% or at least 98% sequence identity to any of SEQ ID NOS:

1-10, and in some examples are 19-31 nucleotides in length, such as 19, 20, 21, 22, 23, 24, 25, 26, 27, 28, 29, 30, or 31 nucleotides in length. In some examples, the primers shown in SEQ ID NO: 1-10 include 1, 2, 3, 4, or 5 nucleotide changes (such as nucleotide substitutions, deletions, additions, or combinations thereof) at any position that is not the final 1 to 5 nt (or in some examples 3 to 5 nt) on the 3'-end, such as the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, or $15^{th}$, nucleotide of the primer (e.g., 1, 2, 3, 4, or 5 nucleotide substitutions in any of nucleotides 1-15 of SEQ ID NO: 1-10). Table 3 shows the disclosed sequences, the total number of nucleotides in the primer, the nucleotide positions where changes should not be made, and the nucleotide positions where a few changes could be made.

TABLE 3

Variations to SEQ ID NOS: 1-10

| Sequence (SEQ ID NO:) | total # nt | Changes not tolerated | Changes tolerated |
|---|---|---|---|
| TGAARGAITGYACTGARAGRCAGGCTAAT (1) | 29 | Any of nucleotides 27-29, and in some examples 25 and 26 | Any of positions 1-24 |
| ACTGARAGRCAGGCTAATTTTTTAG (2) | 25 | Any of nucleotides 23-25, and in some examples 21 and 22 | Any of positions 1-20 |
| TAGGGARAATYTGGCCTTCC (3) | 20 | Any of nucleotides 18-20, and in some examples 16 and 17 | Any of positions 1-15 |
| ATCCCTGCATAAATCTGACTTGC (4) | 23 | Any of nucleotides 21-23, and in some examples 19 and 20 | Any of positions 1-18 |
| CTTTARCTTCCCTCARATCACTCT (5) | 24 | Any of nucleotides 22-24, and in some examples 20 and 21 | Any of positions 1-19 |
| CTTCTGTATGTCATTGACAGTCC (6) | 23 | Any of nucleotides 21-23, and in some examples 19 and 20 | Any of positions 1-18 |
| AGTCCTATTGARACTGTRCCAG (7) | 22 | Any of nucleotides 20-22, and in some examples 18 and 19 | Any of positions 1-17 |
| TTTYTCTTCTGTCAATGGCCA (8) | 21 | Any of nucleotides 19-21, and in some examples 17 and 18 | Any of positions 1-16 |
| CAGTACTGGATGTGGGRGAYG (9) | 21 | Any of nucleotides 19-21, and in some examples 17 and 18 | Any of positions 1-16 |
| TACTAGGTATGGTAAATGCAGT (10) | 22 | Any of nucleotides 20-22, and in some examples 18 and 19 | Any of positions 1-17 |

In some examples, the isolated nucleic acid molecules (such as any of SEQ ID NOS: 1-10, or a sequence at least 90%, at least 95%, at least 97% or at least 98% identical to any of SEQ ID NOS: 1-10), include a label. Exemplary labels include radioactive isotopes, ligands, chemiluminescent agents, fluorophores, haptens, and enzymes.

Kits

The present disclosure provides kits that include one or more of the nucleic acid molecules provided herein, such as those described above. For example, the kit can include primers that permit amplification of HIV-1 nucleic acid molecules, such as one or more of SEQ ID NOS: 1-6, for example in combinations with primers that can be used for sequencing (e.g., SEQ ID NOS: 5-10). For example, the kit can include forward and reverse primers, such as one or more of SEQ ID NOS: 1, 2, 3 and 5, and one or more of SEQ ID NOS: 4 and 6.

In some examples, the kit also includes primers used to sequence the HIV-1 pol region that includes RT and PR, for example to determine the genotype of HIV-1 present in a test sample. For example, the kit can include one or more of SEQ ID NOS: 5-10.

In one example, a kit includes one or more of the primer sequences that comprises or consists of SEQ ID NO: 1, 2, 3, 4, 5, 6, 7, 8, 9 or 10. In another example, a kit includes one or more of the primer sequences that have at least 90%, at least 95%, at least 97%, at least 98%, or at least 99% sequence identity a nucleic acid sequence shown in SEQ ID NO: 1, 2, 3, 5, 7, 8, 9 or 10, wherein the degenerate oligonucleotide is 18 to 32 or 20 to 30 nucleotides in length. Such primers can include a label.

In a particular example, the kit includes 2, 3, 4, 5, 6, 7, 8, 9, or 10, of the disclosed nucleic acid primers, such as a kit that includes SEQ ID NO: 1, for example a kit that includes SEQ ID NOS: 1, 2 and 4, a kit that includes SEQ ID NO: 1, 2, and 3, a kit that includes SEQ ID NO: 1, 2, 3 and 4, a kit that includes SEQ ID NOS: 5-10, a kit that includes SEQ ID NOS: 1-10, a kit that includes SEQ ID NOS: 4-10, or a kit that includes SEQ ID NOS: 5 and 6. Exemplary combinations of primers that can be included in a kit are shown in the Table below. However, one skilled in the art will appreciate that the primer in the kit can include other combinations in addition to the particular combinations disclosed herein.

| Kit Number | SEQ ID NOS: Present |
| --- | --- |
| 1 | 1, 2, 4 |
| 2 | 1, 2, 3 |
| 3 | 1, 2, 4-10 |
| 4 | 1-4 |
| 5 | 5, 6 |
| 6 | 1, 2, 4, 5, 6 |
| 7 | 1, 4, 5, 6 |
| 8 | 2, 4, 5, 6 |
| 9 | 1-6 |
| 10 | 5-10 |
| 11 | 1-10 |
| 12 | 4-10 |

In addition to nucleic acid molecules, the kits can further include one or more agents for performing reverse transcription (such as reverse transcriptase), reagents for performing RT-PCR (such as DNA polymerase and Taq polymerase), reagents for sequencing a nucleic acid molecule, or combinations thereof. Thus, for example, the kits provided herein can further include one or more of reverse transcriptase, Taq polymerase, DNA polymerase, dNTPs, buffers, and the like.

In one example the kits also include materials for collecting a blood sample, such as sterile blood collection tubes (such as those containing EDTA anticoagulant), needles, filer paper to prepare dried blood spot samples, or combinations thereof. In one example the sterile blood collection tubes are vacutainer. In one example the filter paper is Whatman 903 filter paper.

In some examples, the kits further include materials to permit detection of HIV-1 viral load of the subject.

EXAMPLE 1

Materials and Methods

Samples

A total of 381 samples were used: 151 samples used for validation and 230 for application. For validation, 111 HIV-1 positive plasma and 10 dried blood spots (DBS) samples were included as well as 30 HIV-1 negative DBS samples. For application, 132 plasma and 98 DBS samples were tested. The detailed information on these samples is described in Table 4.

TABLE 4

Summary of samples including plasma and dried blood spots (DBS) used.

| Origin | No. of samples | Type of sample | Collection year | ARV status | Median VL$_{log10}$ (range) | Storage condition | VL measurement |
| --- | --- | --- | --- | --- | --- | --- | --- |
| Samples For validation (n = 151) | | | | | | | |
| Cameroon | 38 | Plasma | 2006-2007 | Experienced | 4.05 (2.60-5.57) | −70° C. | Roche Amplicor v1.5 |
| Thailand | 31 | Plasma | 2005 | Naïve | 4.65 (3.14-5.58) | −70° C. | Roche COBAS TaqMan |
| Zambia | 27 | Plasma | 2006-2007 | Experienced | 4.26 (3.34-5.88) | −70° C. | Roche Amplicor v1.5 |
|  | 30$^a$ | DBS | 2005-2006 | Not applicable | Not applicable | −70° C. | Not applicable |
| PT panels | 15 | Plasma | 2009-2010 | Unknown | 4.13 (3.93-4.75) | −70° C. | Unknown |
|  | 10 | DBS | 2010 | Unknown | 3.78 (3.23-4.29) | −70° C. or 5 DBS shipped at ambient | Unknown |
| Samples for application (n = 230) | | | | | | | |
| Vietnam | 72 | Plasma | 2007-2008 | Naïve | Not done | −70° C. | Not done |
|  | 72$^b$ | DBS | 2007-2008 | Naïve | Not done | −70° C. | Not done |

TABLE 4-continued

Summary of samples including plasma and dried blood spots (DBS) used.

| Origin | No. of samples | Type of sample | Collection year | ARV status | Median VL$_{log10}$ (range) | Storage condition | VL measurement |
|---|---|---|---|---|---|---|---|
| Malawi | 34 | Plasma | 2009 | Experienced | 4.07 (2.25-5.89) | −70° C. | Abbott m2000rt |
| Nigeria | 26 | Plasma | 2009 | Experienced | 4.02 (2.18-6.41) | −70° C. | BioMerieux EasyQ |
|  | 26[c] | DBS | 2009 | Experienced | 3.97 (2.18-5.64) | Room temperature for an average 85 days | BioMerieux EasyQ |

[a]HIV negative specimens collected from pregnant women in Tanzania used for assay specific analysis;
[b]Plasma-matched DBS samples collected from VCT sites in Ho Chi Minh City enrolled in an HIV-1 threshold survey;
[c]Plasma-matched DBS samples collected from patients enrolled in the Nigeria prospective cohort at 12-15 months after commencement of first line antiretroviral drugs enrolled in the HIVDR monitoring survey.

Viral RNA and Total Nucleic Acid Extraction

The QIAamp mini-viral RNA kit (Qiagen, Valencia, Calif.) was used to extract RNA from all plasma samples for validation purpose. Details for viral load (VL) measurement on samples from Cameroon, Thailand and Zambia were described previously [22,24,25]. For Malawi samples, Abbott m2000 automatic sample preparation system (0.2 ml extraction protocol) was used to extract the plasma RNA. For Nigeria and Vietnam plasma and DBS samples, the NucliSens® EasyMAG™ automatic sample preparation system (BioMérieux, Durham, N.C.) was used to extract the plasma RNA and blood total nucleic acid. All assays were performed following the manufacturer's instructions and laboratory standard operating procedures.

RT-PCR and Nested PCR

Sequences of RT-PCR and sequencing primers that were re-designed or modified based on the original assay [22] and HIV-1 sequences available on the Internet at the Los Alamos Database (hiv.lanl.gov) are shown in Table 5.

TABLE 5

Primer sequences.

| Primer name | Sequence (5'→ 3') (SEQ ID NO:) | Location (HXB2) | Purpose |
|---|---|---|---|
| PRTM-F1* | F1a-TGAARGAITGYACTGARAGRCAGGCTAAT (1) | 2057-2085 | RT-PCR, one of mixture components |
|  | F1b-ACTGARAGRCAGGCTAATTTTTTAG (2) | 2068-2092 | RT-PCR, one of mixture components |
| PRTM2-F1 | TAGGGA RAATYTGGCCTTCC (3) | 2090-2109 | Rescue RT-PCR primer |
| RT-R1 | ATCCCTGCATAAATCTGACTTGC (4) | 3370-3348 | RT-PCR |
| PRT-F2 | CTTTARCTTCCCTCARATCACTCT (5) | 2243-2266 | Nested PCR & sequencing |
| RT-R2 | CTTCTGTATGTCATTGACAGTCC (6) | 3326-3304 | Nested PCR & sequencing |
| SeqF3 | AGTCCTATTGARACTGTRCCAG (7) | 2556-2577 | Sequencing |
| SeqR3 | TTTYTCTTCTGTCAATGGCCA (8) | 2639-2619 | Sequencing |
| SeqF4 | CAGTACTGGATGTGGGRGAYG (9) | 2869-2889 | Sequencing |
| SeqR4 | TACTAGGTATGGTAAATGCAGT (10) | 2952-2931 | Sequencing |

*FRTM-F1 is a mixture of primers F1a and F1b at a ratio of 1:1 (w/w)

All primers used were synthesized at CDC Biotechnology Core Facility. One-step RT-PCR was performed in a 50-μl reaction, which consisted of 10 μl of RNA or TNA extracts, 0.16 μM each of primers PRTM-F1 (SEQ ID NO: 1 and 2) and RT-R1 (SEQ ID NO: 4), and 1x SuperScript™ III one step RT/Platinum® Taq high Fidelity Enzyme Mix (Invitrogen, Carlsbad, Calif.). RT-PCR condition was an initial cycle RT step at 50° C. for 45 min and 94° C. for 2 min, and followed by 40 cycles of PCR at 94° C. for 15 sec, 50° C. for 20 sec, 72° C. for 2 mM and an extension at 72° C. for 10 min For nested PCR, 2 μl of RT-PCR product was added to a 50 μl reaction containing 0.12 μM of each of the inner primers PRT-F2 (SEQ ID NO: 5) and RT-R2 (SEQ ID NO: 6), 1x GeneAmp Gold Buffer II, 2 mM $MgCl_2$, 400 μM each dNTP and 2.5 U of AmpliTaq Gold LD DNA polymerase (Applied Biosystems, Foster City, Calif.). After initial denaturation at 94° C. for 4 min, 40 cycles of PCR were performed in GeneAmp 9700 thermocycler with the PCR conditions as 94° C. for 15 sec, 55° C. for 20 sec and 72 for 2 min following an extension at 72° C. for 10 min. In the case of the failed first RT-PCR attempt, PRTM2-F1 (SEQ ID NO: 3) was used as rescue primer to replace PRTM-F1 (SEQ ID NO: 1 and 2) to account for mutations occurring at the primer binding site. The nested PCR product was confirmed by 1% agarose gel electrophoresis with a product size of 1,084 base pairs. Purified PCR products were used for cycle sequencing reaction with BigDye terminator cycle sequencing kit 3.1 (Applied Biosystems).

Sequence Analysis

DNA sequencing of HIV-1 pol was performed in 3730 DNA genetic analyzer (Applied Biosystems). Six sequencing primers overlapping the entire amplicon were used (Table 2). Sequencing raw data was edited with ChromasPro, v1.5 (Technelysium Pty Ltd, Australia) and confirmed by a second technician. To double check for all mixed bases, a web-based sequence analysis tool, ReCall [26], in which minor peak calling was set at 15% of the main peak, was used. To rule out PCR contamination, phylogenetic analyses were performed on all newly obtained sequences by MEGA 4 [27]. Sequence quality was also checked by Stanford HIVdb program. Sequences with frame shifts or stop codons were excluded from data analysis. For transmitted HIVDR surveillance, WHO surveillance drug resistance mutation (SDRM) list was used [28]. For drug resistance monitoring surveys, drug resistance-associated mutations in PR and RT were interpreted using the Stanford Genotypic Resistance Interpretation Algorithm. Pairwise nucleotide sequence identity and discrepancy were analyzed using BioEdit [29].

Sensitivity, Accuracy and Specificity of the Assay

As for HIV-1 drug resistance genotyping, there are no standardized or reference method (gold standard) to evaluate analytic and clinical performance in molecular genotyping for HIV-1 group M subtypes. This method was validated according to WHO/HIVResNet drug resistance guidelines [21,23], including participation in an external quality assessment program (EQA PT panels) and comparing the results between the disclosed method and the original method previously described [22].

Because the validation criteria were difficult to define based on the complexity of samples tested in this multi-subtype evaluation and all currently available assays (commercial or in-house) were unable to genotype 100% of the samples tested [16], the genotyping sensitivity intervals as ≥95% was used for samples with viral load≥3 log copies/ml; accuracy was defined as detection of 99% of known DR mutation codons, and reproducibility/precision was defined as ≥98% nucleotide identities in ≥90% of pairwise comparisons. Sensitivity and reproducibility of the assay were assessed by comparing the current genotyping results from 96 field collected samples of known viral load with those of the original assay [22] from Cameroon, Zambia and Thailand (n=96). The assay was also evaluated using TRUGENE system GL12 (DigitalPT, n=5) and ViroSeq system V 2.8 (VQA PT, n=5). The precision of the assay was evaluated using 4 replicates of VQA plasma panels (n=5) and 3 of 4 replicates were tested with the disclosed assay and the remaining one was tested with TRUGENE. The precision test was performed by three individuals. All sequences generated were further confirmed by a $2^{nd}$ individual and with ReCall online software. In addition, 10 DBS panels shipped at two different temperature conditions from VQA were also tested by the optimized assay. Specificity was determined by testing 30 HIV-negative DBS specimens collected from pregnant women in Tanzania.

Applying the Assay for Surveillance of Transmitted HIVDR and HIVDR Prevention Monitoring Surveys in Resource-limited Countries Seventy two matched plasma and DBS samples from newly HIV-diagnosed persons in Vietnam were tested. For HIVDR monitoring surveys, the disclosed assay was used for resistance testing of samples collected from patients 12-15 months after the commencement of ART in two monitoring surveys. For the Malawi monitoring survey, 34 plasma samples from patients with viral load ranged from 2.25 to 5.89 log 10 copies/ml were tested. In Nigeria monitoring survey, 26 matched plasma and DBS samples with plasma viral load ranged from 2.18 to 6.41 log 10 copies/ml were analyzed.

HIV-1 Subtyping

HIV-1 subtyping for the newly obtained sequences was performed using the REGA 4 HIV-1 Genotyping Tool [30]. A phylogenetic analysis was further conducted using neighbor-joining method for sequences with unclassifiable subtypes. Reference sequences were obtained from the Los Alamos Database.

Reagent Cost Comparison

To estimate reagent cost savings by using the disposed genotyping assay, the reagent cost per test of the assay was calculated and compared with the reagent costs of commercially available genotyping systems, TRUGENE and ViroSeq. Current U.S. market values in dollars were used for all the reagents we used in the in-house assay including RNA isolation, RT-PCR, nested PCR, PCR amplification confirmation and sequencing reactions. This reagent cost estimates did not include the cost for running test controls and any repetitions when needed.

Statistical Analysis

Wilcoxon Signed-Rank test was used to analyze the difference in number of nucleotide mixtures detected between the optimized and the original in-house assays. The statistical significance was considered for P value<0.05.

Ethical Consideration

In accordance with United States regulations and international guidelines, the Centers for Disease Control and Prevention (CDC) human subjects review process determined this activity to be non-research. All the study protocols were approved by local institutional review boards and by the Associate Directors for Science (ADS) of Division of Global HIV/AIDS and Center for Global Health, CDC.

EXAMPLE 2

Validation of the Optimized Assay

This example describes the calculated sensitivity and specificity of the disclosed HIV-1 genotyping assay.

Sensitivity: The sensitivity of the disclosed optimized assay was evaluated with 96 HIV-1 positive plasma samples collected from Cameroon, Thailand and Zambia. Of these, 5 samples with VL<3 log 10 copies/ml and 87 (95.6%) of 91 samples with VL≥3 log 10 copies/ml were genotyped, resulting in overall genotyping rate of 95.8% (92/96) compared to 96.8% (93/96) by the original assay.

Accuracy: The accuracy of the disclosed assay was first assessed by comparing 87 paired nucleotide sequences generated by the original assay [22] and the disclosed assay using ReCall and BioEdit programs. The mean nucleotide identity was 99.3±0.50% (mean±SD) among paired nucleotide sequences. Wilcoxon signed-rank test was used to compare original and disclosed assays in basecalling nucleotide mixtures and revealed that the disclosed assay detected significantly more nucleotide mixtures than the original assay (P<0.001). However, this difference did not translate into differences in HIVDR mutations. Among 144 drug resistant (DR) mutations detected in paired samples, complete discordant mutations at DR mutation sites were not detected and only 11 partially discordant DR mutation sites including 3 in PR and 8 in RT (Table 6) were observed. The overall DR codon agreement was 99.75% between the 87 paired samples

TABLE 6

Discordant drug resistance-associated amino acid positions in protease and RT from 87 plasma samples[a] genotyped by the original and disclosed assays

| Amino acid position | Mutation | Amino acid detected in original assay (No. of samples) | Amino acid detected in the disclosed assay | No. partially discordant mutation |
|---|---|---|---|---|
| Protease | | | | |
| 32 | V32A | V (87) | V (86), AV (1) | 1 |
| 33 | L33F | L (84), F (3) | L (84), F (3) | 0 |
| 35 | E35G | G (86), EG (1) | G (85), EG (2) | 1 |
| 71 | A71V | A (86), V (1) | A (86), AV (1) | 1 |
| 74 | T74S | T (82), S (5) | T (82), S (5) | 0 |
| Reverse Transcriptase | | | | |
| 62 | A62V | A (86), AV (1) | A (86), AV (1) | 0 |
| 65 | K65R | K (86), R (1) | K (86), KR (1) | 1 |
| 67 | D67N | D (86), DN (1) T (82), ST (1), N (1), | D (86), DN (1) T (82), ST (1), N | 0 |
| 69 | T69S/N | NT (3) | (1), NT (3) | 0 |
| 90 | V90I | V (85), I (1), IV (1) | V (85), IV (2) | 1 |
| 98 | A98G | A (86), G (1) | A (86), G (1) | 0 |
| 101 | K101E/Q | K (84), E (2), Q (1) | K (84), E (2), Q (1) K (76), N (8), KN | 0 |
| 103 | K103N | K (77), N (8), KN (2) V (82), A (1), I (3), | (3) | 1 |
| 106 | V106A/I | IV (1) | V (83), A (1), I (3) | 1 |
| 118 | V118I | V (83), I (3), IV (1) | V (83), I (3), IV (1) | 0 |
| 138 | E138A | E (86), A (1) V (82), D (3), DV | E (86), A (1) V (82), D (3), DV | 0 |

TABLE 6-continued

Discordant drug resistance-associated amino acid positions in protease and RT from 87 plasma samples[a] genotyped by the original and disclosed assays

| Amino acid position | Mutation | Amino acid detected in original assay (No. of samples) | Amino acid detected in the disclosed assay | No. partially discordant mutation |
|---|---|---|---|---|
| 179 | V179D/T | (1), T (1) | (1), T (1) Y (81), C (3), CY | 0 |
| 181 | Y181C | Y (80), C (3), CY (3), M (78), V (8), IMV | (3) M (78), V (8), IMV | 0 |
| 184 | M184V | (1) | (1) | 0 |
| 188 | Y188C/L | Y (86), L (1), CY (1) | Y (86), L (1) G (83), A (2), AG | 1 |
| 190 | G190A | G (84), A (3) | (2) | 1 |
| 210 | L210F | L (86), F (1) | L (86), F (1) | 0 |
| 215 | T215A | T (86), AT (1) | T (87) | 1 |
| 221 | H221Y | H (87) | H (86), HY (1) | 1 |

[a]Five samples that did not generate full-length sequences for protease (codon 6 to 99) and reverse transcriptase (codon 1 to 251) were excluded for the analysis.

Testing 10 plasma PT panel samples (five from AccuTest and five from VQA) using the disclosed and TRUGENE or ViroSeq assay also indicated that the disclosed assay detected more nucleotide mixtures than commercial kits. However, the DR mutation site differences only occurred in 2 of the 76 DR mutations between the disclosed assay and Trugene and 2 of the 44 between the disclosed assay and Viroseq in mixture bases. The overall sequence identity was 99.6±0.41% between disclosed assay and TRUGENE, and 99.1±0.65% between the disclosed assay and ViroSeq (Table 7).

TABLE 7

Pairwise sequence identity analysis between the disclosed and TRUGENE or ViroSeq assays

| Sequence comparison | Analysis results |
|---|---|
| AccuTest PT panel | Disclosed vs TRUGENE |
| No. of sample | 5 |
| % nucleotide identity | 99.6 ± 0.40 |
| Mean nucleotide mixtures | 11.4 vs 6.2 |
| % amino acid identity | 98.9 ± 0.48 |
| No. DR mutations | 76 vs 74 |
| Partial discordant mutation (%) | 2/76 (2.6) |
| VQA PT panel | Disclosed vs ViroSeq |
| No. of sample | 5 |
| % nucleotide identity | 99.1 ± 0.65 |
| Mean nucleotide mixtures | 26.4 vs 18.8 |
| % amino acid identity | 97.51 ± 1.75 |
| No. DR mutation mutations | 44 vs 42 |
| Partial discordant mutation (%) | 2/44 (4.5) |

To demonstrate that more sensitive detection of base mixtures in the disclosed assay is a reproducible event, 4 replicates of 5 samples were analyzed that were tested by three disclosed assay runs and one TRUGENE run under different operators. Highly concordant sequence identities ranging from 98.22% to 99.65% were observed. The minor differences observed in sequence identity were caused by base mixtures (Table 8).

TABLE 8

Genotyping reproducibility of replicate PCR products generated from independent RT-PCR amplification process by 3 different technicians on a 5-member proficiency testing panel received from VQA.

| Sample ID | HIV-1 VL (log10) | HIV-1 Subtype | % Nucleotide sequence identity | No. of drug resistance mutations |  |  |  | No. Partially discordant mutation |
|---|---|---|---|---|---|---|---|---|
|  |  |  |  | Replicate Tests |  |  |  |  |
|  |  |  |  | IH1* | IH2 | IH3 | TG# |  |
| 1 | 3.76 | B | 98.83 ± 0.18 | 1 | 1 | 1 | 1 | 0 |
| 2 | 4.13 | C | 99.65 ± 0.23 | 10 | 10 | 7 | 10 | 3 |
| 3 | 4.19 | F | 98.22 ± 0.30 | 0 | 0 | 0 | 0 | 0 |
| 4 | 3.93 | B | 99.08 ± 0.11 | 5 | 5 | 5 | 5 | 0 |
| 5 | 4.75 | C | 99.58 ± 0.08 | 6 | 6 | 5 | 4 | 3 |

*IH1-3: tests were independently performed by 3 technicians using the disclosed assay;
TRUGENE system.

Figure 2A:
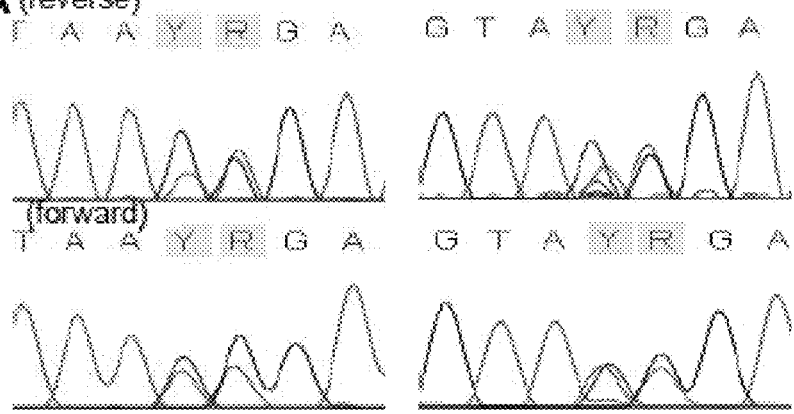
FIGS. 2A-2C are graphs showing the difference of mixture chromatographs independently generated by 3 different operators using the optimized in-house assay from one of the PT samples. (A) shows 2 codons (37 and 41 of RT) with nucleotide base calling of AYR and AYR; (B) shows the AWR at codon 41 (the second peaks at codon 37 were not detected in this reaction); (C) shows ACR at codon 37 (minor T was not flagged by the ReCall at the cutoff of 15%) and AHR at codon 41 (almost equal height of second and third peak at the $2^{nd}$ position).
Figure 2B:
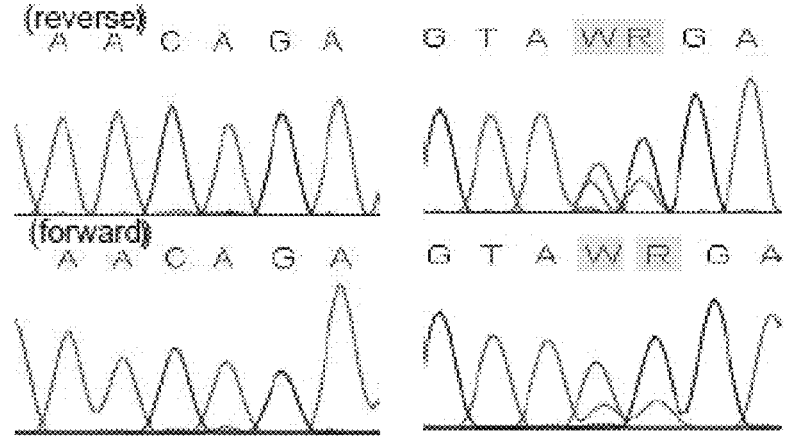
Figure 2C:
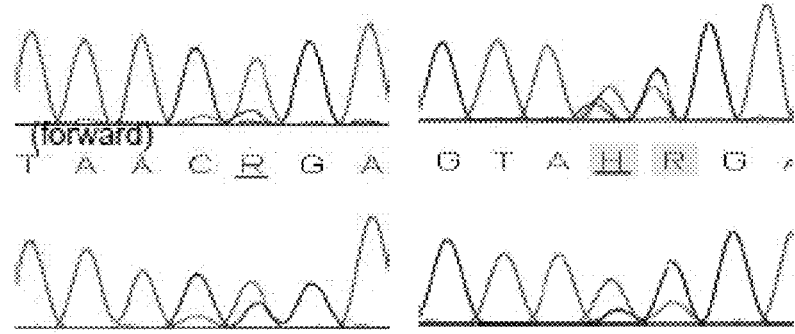

For example, at codons 37 and 41 of RT in sample 3 (FIG. 1), one replicate detected mixture RY at the $2^{nd}$ and $3^{rd}$ positions of codon 37, and the second replicate did not find any mixtures, while the third replicate showed lower, yet visible, second peaks compared to the first replicate (FIGS. 2A-C). Similarly at the $2^{nd}$ position of codon 41, the first replicate revealed a Y (C/T), the second replicate showed a W (A/T), and the third replicate revealed a H (A/C/T) while TRUGENE replicate detected a Y (C/T). Nucleotide mixtures also caused some mismatched DR mutations between the replicates. For instance, one in-house replicate missed 3 mixed codons (K65KR, D67DN and T69IT) in sample 2 among the 4 replicates. However, the minor peaks of nucleotide bases at these three codons could be seen, but were below the mixture cutoff (15%) on the chromatogram by ReCall. Thus these mixtures were not counted and resulted in the sequence discrepancy. Another partial discordant example was the DR mutation M184MV, which was detected in sample 5 by all 3 in-house replicates but not found in TRUGENE replicate. These results indicated that the sequences generated by population-based sequencing were highly reproducible but the sensitivity at detecting low frequency of drug resistant HW variants was challenging.

Sensitivity on DBS samples: DBS samples are recommended by WHO for HIVDR surveillance in resource-limited settings in treatment-naïve populations [21]. The assay sensitivity with two matched DBS experimental panels shipped under different temperature conditions from VQA was evaluated. The disclosed assay was able to genotype all 5 DBS samples shipped with dry ice and 4 of 5 DBS samples shipped at ambient temperature with DBS VL ranging from 3.17 to 3.98 log 10 copies/ml. The failed sample GEN001BS.04C was the sample with the lowest VL of 3.17 log 10 copies/ml (Table 9).

TABLE 9

Genotyping efficiency and drug resistance mutations identified by the disclosed assay from DBS PT panels

| Panel sample ID | Shipping conditions | Plasma VL (Log10) | DBS VL (Log10) | RT-PCR result | Subtype | Drug resistance PR | RT |
|---|---|---|---|---|---|---|---|
| DBS panel A |  |  |  |  |  |  |  |
| GEN001BS.01 A | Dry ice | 3.78 | 3.51 | + | F | None | None |
| GEN001BS.02 A | Dry ice | 3.73 | 3.76 | + | B | None | M184MV, K103N |
| GEN001BS.03 A | Dry ice | 4.29 | 3.98 | + | C | None | M41L, K103N, M184V, T215Y |
| GEN001BS.04 A | Dry ice | 3.23 | 3.17 | + | B | L10I, L23I, L33F, M46L, I54V, A71T, V82A, N88G, L90M | M41L, E44D, A62V, D67N, L74V, L100I, K103N, L210W, T215Y, H221Y |
| GEN001BS.05 A | Dry ice | 3.87 | 3.80 | + | B | None | K103N, Y181C, P225H |
| DBS panel C |  |  |  |  |  |  |  |
| GEN001BS.01 C | Ambient | 3.78 | 3.51 | + | F | None | None |
| GEN001BS.02 C | Ambient | 3.73 | 3.76 | + | B | None | M184MV, K103N |
| GEN001BS.03 C | Ambient | 4.29 | 3.98 | + | C | None | M41L, K103N, Y181CY, M184MV, T215Y |
| GEN001BS.04 C | Ambient | 3.23 | 3.17 |  | N/A* | NA | NA |
| GEN001BS.05 C | Ambient | 3.87 | 3.80 | + | B | None | K103N, Y181CY, P225H |

*N/A: not available; bold and underlined residues were partially discordant resistance mutations from paired DBS shipped under different temperature conditions.

To evaluate the specificity of the optimized in-house assay, HIV negative DBS samples (n=30) collected from women attending ANC clinics in Tanzania were tested and were found to be negative, resulting in the assay specificity of 100%.

EQA assessment results: Based on WHO/HIVResNet requirement to pass the PT panels, a drug resistance mutation (DRM) site score and nucleotide (nt) alignment score with consensus sequence of at least 99% (considering all 5 samples) must be achieved. The disclosed assay has passed two sets of plasma PT panels with 100% DRM, 99.98% nt and 100% DRM, 99.88% nt scores, respectively. The assay showed high sequence concordance with the labs participating in WHO EQA program.

EXAMPLE 3

Use of Assay in the Surveillance of HIVDR in Resource-Poor Countries

With the satisfactory validation results of the disclosed assay, it was applied in the surveillance of HIVDR in three PEPFAR-supported countries.

tially discordant (7.54%) and only 2.05% were completely discordant.

EXAMPLE 4

HIV-1 Subtypes

Phylogenetic analysis revealed that the overall subtype distributions among the 236 newly obtained sequences were 43.6% CRF 01_AE, 25.6% C, 13.1% CRF02_AG, 5.1% G, 4.2% B, 2.5% A, 2.1% F, 2.1% unclassified (UC), and 0.4% each CRF06_CPX, CRF09_CPX and CRF-07_BC. Subtype distributions are different from country to country, for instance, all samples tested from Vietnam and Malawi were CRF-01_AE and subtype C, respectively, while multiple subtypes were identified from samples collected from Cameroon, Canada and Nigeria (Table 10).

TABLE 10

Subtypes and CRFs genotyped by the disclosed assay

| Sample source | No. of Sample | A | B | C | F | G | CRF01_AE | CRF02_AG | CRF06_CPX | CRF07_BC | CRF09_CPX | UC |
|---|---|---|---|---|---|---|---|---|---|---|---|---|
| Cameroon | 31 | 3 | | | 2 | 2 | 21 | | | | 1 | 2 |
| Malawi | 32 | | | 32 | | | | | | | | |
| Nigeria | 25 | 1 | | | | 10 | | 10 | 1 | | | 3 |
| Zambia | 25 | 1 | | 24 | | | | | | | | |
| Thailand | 31 | | | | | | 31 | | | | | |
| Vietnam | 72 | | | | | | 72 | | | | | |
| Canada, US (PT) | 20 | 1 | 10 | 5 | 3 | | | | | 1 | | |
| Total | 236 | 6 | 10 | 61 | 5 | 12 | 103 | 31 | 1 | 1 | 1 | 5 |
| % subtype | 100 | 2.54 | 4.24 | 25.85 | 2.12 | 5.09 | 43.64 | 13.14 | 0.42 | 0.42 | 0.42 | 2.12 |

Threshold survey of transmitted HIVDR in recently HIV-infected population in Vietnam: 72 plasma and matched DBS specimens collected from individuals attending voluntary counseling and testing (VCT) in Ho Chi Minh City were tested. All 72 plasma and 69 (96%) DBS samples were genotyped and sequence identity analysis (n=69) indicated that overall nucleotide identity was 98.9%±0.62% between matched plasma and DBS samples. The sequence differences were caused by partially discordant mixture bases located in the three HIVDR codons in the RT region.

Detection of HIVDR development in ART-experienced patients from Malawi and Nigeria: The disclosed assay was used to detect HIVDR development in patients treated with first-line ARVs for 12-15 months in two monitoring surveys conducted in Malawi (n=34) and Nigeria (n=26). Genotyping was successful for all 46 plasma samples collected from virologically failed patients defined as VL≥3 log 10 copies/ml according to WHO definition [4]. For patients with VL between 2.18 and ≤3 log 10 copies/ml, 78.6% (11/14) plasma samples (7/8 from Nigeria and 4/6 from Malawi) were also successfully, all 18 matched DBS samples from virologically failed patients and 4 of the 8 DBS samples with VL between 2.18 and ≤3 log 10 copies/ml from Nigeria were genotyped. The nucleotide sequence identity between the 22 plasma and DBS pairs was 98.8±0.80%. For DR mutation, 90.4% DR mutations identified in plasma were also identified in DBS. Among the 9.6% discordant DR mutations between plasma and DBS samples, the majority was par-

EXAMPLE 5

Reagent Cost Comparison

Using the current U.S. market values in dollars for all the reagents used in the disclosed assay, the reagent cost per test for the disclosed assay was calculated to be $40.00, compared to $213.20 for TRUGENE and $172.86 for ViroSeq. In this reagent cost calculations, the cost for assay controls and any need for repetition of tests were not included, but would increase the cost of reagents for all the assays compared here.

EXAMPLE 6

Dried Blood Spots are Suitable for HIV-1 Viral Load Measurement and Drug Resistance Genotyping This example describes methods used to demonstrate that dried blood spots (DBS) are a suitable alternative sample type for HIV-1 viral load measurement and drug resistance genotyping in patients receiving first-line antiretroviral therapy. This example compared dried fluid spots to the gold standard plasma for viral load testing and HIV drug resistance genotyping. The results shown herein demonstrate that DBS could be used for monitoring viral load and drug resistance in ART-patients in resource-limited settings.

Materials and Methods

Participants

Between January and July, 2008, 281 HIV-1-infected patients who were eligible for ART were consecutively enrolled into the monitoring survey from two ART sites in Abuja, Federal Capital Territory, Nigeria and they were treated with the standard first-line antiretroviral drugs (ARVs) following the Nigeria National Treatment Guidelines [48]. Patients were monitored for clinical improvement and CD4 T-lymphocyte count during the one year follow-up (defined as 12-15 months after the initiation of ART) according to the routine practice of the sites. At the 12 month follow-up visit, 176 patients attended their visits at the two sites and blood was collected from each of them. One hundred seventy three patients were included in the current study and three patients were excluded due to insufficient sample volumes in two patients and mislabeling in one patient. The detailed clinical and demographic information of participants has been described elsewhere [49].

Specimen Collection, Preparation, and Storage

Ten milliliters of whole blood was collected into an EDTA vacutainer tube from each of the 173 patients who visited the ART sites at one year after initiation of ART. DBS were prepared by spotting 100 µl of whole blood onto each of the five preprinted circles on a Whatman 903 filter paper (Whatman Inc, Piscataway, N.J.). Plasma was then separated from blood cells by centrifugation and used to make dried plasma spot (DPS) with 50 µl/spot following the same instruction for DBS preparation, and the remainder stored immediately at −70° C. for the gold standard specimens. Both DBS and DPS cards were allowed to dry overnight at ambient temperature. The next day, glassine paper was folded around each DBS or DPS card, and 10-20 cards were packaged in a Bitran bag with desiccant packs and a humidity indicator card, and stored at ambient temperature for an average of 85.31±42.66 days (median 83.5 days) before they were shipped to WHO Specialized Drug Resistance Laboratory at the Centers for Disease Control and Prevention (CDC), Atlanta, Ga., U.S. for testing. All specimens were stored at −80° C. upon arrival at CDC.

Nucleic Acid Extraction and HIV-1 Viral Load Analysis

One DBS or DPS spot was cut out per specimen and placed in a 2 ml of NucliSENS® lysis buffer (Biomeriuex, Durham, N.C.) for 30 min at room temperature with gentle rotation. Plasma specimens (200 µl) were added to 2 ml of NucliSENS® lysis buffer and incubated for 10 min at room temperature. Nucleic acid was then extracted from all specimens using the NucliSENS® EasyMag® (Biomeriuex, Durham, N.C.) automated extraction system following the manufacturer's instructions. Nucleic acid was eluted in 25 µl of NucliSENS® Extraction Buffer 3 and stored at −80° C. until use.

HIV-1 viral load (VL) was determined by the NucliSENS EasyQ® automated system using NucliSENS EasyQ® HIV-1 v1.1 RUO test kits (Biomeriuex, Durham, N.C.) following the manufacturer's instructions. The linear range of this assay is 50-3,000,000 copies/ml when 1 ml of plasma is used [50]. The VL for all specimens was normalized to a volume of 1 ml of plasma. The amount of plasma in DBS was determined by normalizing for the volume of the sample and the mean hematocrit (a generalized value of 40%) as described previously [51].

HIV-1 Drug-Resistance Genotyping

Genotyping of the protease and RT regions of the HIV-1 pol gene was performed using the broadly sensitive genotyping assay described in Example 1 [22, 52]. Briefly, a 1,084 base pair segment of the 5' region of the pol gene was generated by RT-PCR followed by nested PCR. This fragment was purified, sequenced using the BigDye® Terminator v3.1 Cycle Sequencing Kit (Applied Biosystems, Foster City, Calif.), and analyzed on the ABI Prism™ 3730 Genetic Analyzer (Applied Biosystems). ChromasPro version 1.42 (Technelysium Pty Ltd, Tewantin, Australia) was used to edit the raw sequences and generate consensus sequences. HIV drug-resistance mutations were determined using Stanford University Drug Resistance Database.

Statistical Analysis

All HIV-1 VL values were log 10 transformed before analysis. Quantitative variables are expressed as means (±SD) and (95% confidence intervals) where relevant. Wilcoxon signed-rank test was used to assess the bias in measuring VL between plasma and DBS or DPS. Bland-Altman analysis was used to determine concordance between VL measurements of plasma and DBS or DPS [53]. The agreement for the detection of virological failure by DBS or DPS and plasma was assessed using kappa-statistics and p-values were determined using Fisher's exact test. As suggested by Fleiss, Kappa values<0.40 were considered to be poor agreement, values>0.40 and <0.75 were considered fair to good agreement, and those >0.75 meant excellent agreement [54]. Genotyping efficiency was determined by dividing the number of samples successfully genotyped by the total number of samples with a detectable VL or VL≥1,000 copies/ml. Nucleotide identity was calculated using BioEdit sequence alignment editor (Carlsbad, Calif.). Statistical calculations were performed using GraphPad Prism (version 5.0, GraphPad Software, La Jolla, Calif.) or SPSS software (version 17.0, SPSS Inc. Chicago, Ill.).

Results

HIV-1 Viral Load (VL) Analysis

Using the NucliSens HIV-1 v1.1 RUO kit and the NucliSens EasyQ analyzer, HIV-1 VL was measured in parallel plasma, DBS and DPS specimens collected from all the 173 patients at 12 months after the initiation of ART. Viral load analysis revealed that 26 plasma, 28 DBS, and 17 DPS specimens had detectable VL. The mean log 10 VL (±SD) for plasma, DBS, and DPS were 3.78±1.1 (range 2.18-6.41), 3.63±0.88 (range 2.64-5.56), and 3.85±0.82 (range 2.92-5.94), respectively. When the mean VL of specimens that had a detectable VL was compared in plasma and DBS or plasma and DPS (matched specimens), no statistical difference was found between plasma and DBS VL values (P=0.0619); however VL values from matched plasma and DPS were significantly different (P=0.0007). Bland-Altman agreement analysis revealed that DBS and DPS were comparable blood collection methods to plasma in VL measurement, as the difference between plasma and DBS/DPS VL values for all but one specimen are within the 95% limits of agreement (FIGS. 3A & 3B). Notably, the mean difference for plasma and DPS was above 0.5 and all but one of the data points were above zero, indicating that plasma VL values were consistently higher than DPS VL values by an average of 0.5 log 10 copies/ml (FIG. 3B). In contrast the mean difference between plasma and DBS was closer to zero and the points were more evenly distributed above and below zero compared to DPS.

To assess the feasibility of using DBS and DPS for WHO-recommended HIVDR monitoring surveys, the ability of these dried-form blood collection methods was evaluated to detect virological failure, defined as plasma viral RNA level of ≥1,000 copies/ml as recommended by WHO [4], using plasma as the gold standard. Table 11 illustrates that there is excellent overall agreement between DBS/DPS and plasma in detecting virological failure in ART patients, with a P value<0.001 for both DBS and DPS and a Kappa statistics of 0.78 (DBS) and 0.83 (DPS). DBS were able to correctly define virological failure in 14 out of 18 patients (77.8%), and viral suppression was correctly identified in DBS for 152 of the 155 patients (98.1% specificity and 97.4% negative predictive value). Likewise, DPS were capable of defining virological failure in 14 of 18 patients and viral suppression for 154 of 155, resulting in a positive and negative predictive value of 93.3% and 97.5%, respectively.

Stanford University HIV Drug Resistance Database using plasma as the gold standard w34 compared. DPS were not included in this analysis due to the poor genotyping rate (Table 12). Table 13 provides a detailed view of drug resistance mutations identified from 22 matched (genotyped in both DBS and plasma) and 3 unmatched (genotyped in plasma only) plasma and DBS specimens that were geno-

TABLE 11

Concordance between DBS, DPS, and plasma in diagnosing virological failure as defined as plasma viral RNA level equal or greater than 1,000 copies/ml.

| | | Plasma | | | | | Performance of |
|---|---|---|---|---|---|---|---|
| | | ≥1000 | <1000 | Total | Kappa | P | DBS and DPS |
| DBS | ≥1000 | 14 | 3 | 17 | 0.78 ± | <0.001 | Sensitivity = 77.8% |
| | <1000 | 4 | 152 | 156 | 0.08SE | | Specificity = 98.1% |
| | Total | 18 | 155 | 173 | (0.62-0.94) | | PPV$^a$ = 82.3% |
| | | | | | | | NPV$^a$ = 97.4% |
| DPS | ≥1000 | 14 | 1 | 15 | 0.83 ± | <0.001 | Sensitivity = 77.8% |
| | <1000 | 4 | 154 | 158 | 0.07SE | | Specificity = 99.4% |
| | Total | 18 | 155 | 173 | (0.69-0.98) | | PPV$^a$ = 93.3% |
| | | | | | | | NPV$^a$ = 97.5% |

$^a$Positive predictive value (PPV) and negative predictive value (NPV) were calculated using 10.4% prevalence of virological failure.

Drug Resistance Genotyping of HIV-1 Pol Gene Region

To assess whether DBS and DPS were comparable to plasma for HIV drug resistance (DR) genotyping in ART-experienced patients, the genotyping efficiency was determined for DBS and DPS specimens and stratified the data by plasma VL, as well as the nucleotide sequence identity to plasma for DBS and DPS specimens that yielded genotyping results in both plasma and the paired dried fluid spot. The ability to successfully genotype specimens with a VL≥1,000 copies/ml was 100% in plasma and DBS; however was only 38.9% in DPS (Table 12). Despite having a substantially reduced genotyping rate, the sequences obtained from DPS had a high nucleotide sequence identity with sequences obtained from plasma specimens (Table 12). DBS had a comparable nucleotide sequence identity, showing 98.6% identity to plasma at plasma VL<1,000 copies/ml and 98.8% at VL≥1000 copies/ml (Table 12).

typed. In total, 78 drug resistance mutations were identified in the matched plasma specimens, 68 of which were also detected in DBS. All of the discordant mutations present in plasma and absent in corresponding DBS were the result of base mixtures (2 A98AG, H221HY, K101KQ), indicating the presence of a sub-dominant population of virus undetectable in DBS. Analysis of ARV susceptibility profiles determined by the HIVdb algorithm created by the Stanford Database indicates that majority of the discordant drug resistance mutations between matched plasma and DBS did not lead to changes in drug susceptibility profiles. However, 3 matched and 1 unmatched specimens were identified with significant differences in drug-susceptibility, 3 of which were below a plasma VL of 1,000 copies/ml. The one discordant specimen in this group with a clinically relevant

TABLE 12

Dried fluid spot genotyping efficiency and pairwise nucleotide identity compared to plasma specimens

| | Plasma | DBS | | DPS | |
|---|---|---|---|---|---|
| Plasma VL group | Genotyping efficiency | Genotyping efficiency | Nucleotide Identity to plasma | Genotyping efficiency | Nucleotide Identity to plasma |
| <1,000 copies/ml | 87.5% (7/8) | 50.0% (4/8) | 98.6 ± 1.2% (96.7 to 100.5%) | 12.5% (1/8) | 98.9%$^a$ |
| ≥1,000 copies/ml | 100% (18/18) | 100% (18/18) | 98.8 ± 0.83% (98.4 to 99.2%) | 38.9% (7/18) | 98.2 ± 1.1% (97.2 to 99.2%) |

$^a$Represents the VL of one DPS sample and is not a mean VL

HIV-1 Drug Resistance Mutation Profile

To further analyze HIVDR genotyping in plasma and DBS, drug resistance mutation profiles determined by the VL of ≥1,000 copies/ml had detectable drug resistance in the DBS specimen due to K65R mutation which was not detected in plasma.

TABLE 13

Mutation Profiles of plasma and DBS specimens

| Matched Specimens | Specimen ID | ARV Regimen | Plasma PI | NRTI | NNRTI |
|---|---|---|---|---|---|
| Concordant Specimens | 2-2-063 | AZT, 3TC, NVP | | | K101E, E138A, G190A |
| | 1-2-095 | 3TC, d4T, NVP | | T69ST | |
| | 2-2-028 | AZT, 3TC, NVP | | | G190A |
| | 2-2-132 | 3TC, TDF, NVP | | K65R, M184V | Y181C |
| | 1-2-128 | 3TC/AZT, NVP | L10I | V75IV, K219EK | Y181C |
| | 2-2-010 | AZT, 3TC, NVP | | K70R, M184V | A98AG, Y188L |
| ≥1,000 copies/ml | 2-2-041 | FTC/TDF, NVP | | K65R, M184V | L100I, K103N |
| | 1-2-176 | 3TC, d4T, NVP | NO | MUTATIONS | |
| | 1-2-121 | 3TC, d4T, EFV | L10I | | |
| | 2-2-118 | 3TC, d4T, EFV | | V118I, M184V | K103N, P225H |
| | 1-2-030 | 3TC, d4T, NVP | L10IV | | |
| | 1-2-016 | 3TC/AZT, NVP | T74S | | K103KN |
| | 1-2-186 | Unknown | T74S | D67G, K70R, M184V, K219E | A98G, V108I, Y181C |
| | 1-2-102 | 3TC, d4T, NVP | | M184V | K103N, K238EK |
| <1,000 copies/ml | 2-2-091 | AZT, 3TC, NVP | | M184V | K101E, E138A, G190A, M230L |
| Discordant Specimens ≥1,000 copies/ml | *2-2-120 | FTC/TDF, NVP | | D67DN, K70KR, M184V, K219DEKN | A98AG, V179DE, Y181I |
| | 2-2-105 | AZT, 3TC, NVP | L10I | M184MV | K103N |
| | 1-2-100 | 3TC, d4T, NVP | L10I | M184V | A98AG, Y181C, H221HY |
| | 2-2-128 | FTC/TDF, NVP | | M184V | A98G, K101KQ, V108IV, Y181C, H221HY |
| ≥1,000 copies/ml | *2-2-116 | FTC/TDF, NVP | L10I | M184MV | A98G, Y181C, H221Y |
| | *1-2-099 | 3TC, d4T, NVP | | M184V | K103N, V108IV |
| | 2-2-130 | FTC/TDF, NVP | | A62AV, K65KR, M184V, K219KN | K103N, Y181C |
| Unmatched Specimens | *2-2-053 | AZT, 3TC, NVP | | D67DN, K70KR, M184V, T215FIST | Y181C, H221HY |
| <1,000 copies/ml | 1-2-167 | 3TC/AZT, EFV | M46L | | |
| | 2-2-060 | FTC/TDF, EFV | NO | MUTATIONS | |

| Matched Specimens | Specimen ID | DBS PI | NRTI | NNRTI |
|---|---|---|---|---|
| Concordant Specimens | 2-2-063 | | | K101E, E138A, G190A |
| | 1-2-095 | | T69ST | |
| | 2-2-028 | | | G190A |
| | 2-2-132 | | K65R, M184V | Y181C |
| | 1-2-128 | L10I | V75IV, K219EK | Y181C |
| | 2-2-010 | | K70KR, M184V | A98AG, Y188L |
| ≥1,000 copies/ml | 2-2-041 | | K65R, M184V | L100I, K103N |
| | 1-2-176 | NO | MUTATIONS | |
| | 1-2-121 | L10I | | |
| | 2-2-118 | | V118I, M184MV | K103KN, P225HP |
| | 1-2-030 | L10IV | | |
| | 1-2-016 | T74S | | K103KN |
| | 1-2-186 | T74S | D67G, K70R, M184V, K219E | A98G, V108I, Y181C |
| | 1-2-102 | | M184V | K103N, K238E |
| <1,000 copies/ml | 2-2-091 | | M184V | K101E, E138A, G190A, M230L |
| Discordant | *2-2-120 | | K65R, D67N, K70KR, | V179DE, Y181I |

TABLE 13-continued

Mutation Profiles of plasma and DBS specimens

| Specimens | | | | M184V, K219E | |
|---|---|---|---|---|---|
| ≥1,000 copies/ml | 2-2-105 | L10I | M184MV | | K103N, H221HY |
| | 1-2-100 | L10I | M184V | | Y181C, H221Y |
| | 2-2-128 | | M184V | | A98G, V108I, Y181C |
| ≥1,000 copies/ml | *2-2-116 | L10I | | | A98G, Y181C, H221Y |
| | *1-2-099 | NO | MUTATIONS | | |
| | 2-2-130 | | L74V, M184V | | K103N, Y181C |
| Unmatched Specimens | *2-2-053 | NO | PCR | | PRODUCT |
| <1,000 copies/ml | 1-2-167 | NO | PCR | | PRODUCT |
| | 2-2-060 | NO | PCR | | PRODUCT |

Mutation profiles from all plasma specimens that were genotyped are shown along with the corresponding DBS specimen. Matched refers to specimens in which both the plasma and DBS specimens were genotyped; unmatched refers to specimens in which we were only able to genotype the plasma specimen due to poor PCR amplification of the DBS specimen.
Discordant mutations between plasma and DBS specimens are bolded.
*highlights specimens where the plasma and DBS specimens had differing drug susceptibility (SIR) ratings determined by Stanford University HIV Drug Resistance Database HIVdb algorithm.
AZT, zidovudine;
3TC, lamivudine;
FTC, emtricitabine;
TDF, tenofovir disoproxil fumarate;
d4T, stavudine;
EFV, efavirenz;
NVP, nevirapine;
PI, protease inhibitor;
NRTI, nucleoside reverse transcription inhibitor;
NNRTI, non-nucleoside reverse transcription inhibitor.

Discussion

In this example, it is demonstrated that DBS and DPS were comparable to plasma for quantitative VL analysis according to the 95% agreement limits of the Bland-Altman analysis (FIGS. 3A-3B). However DPS displayed a clinically relevant bias of >0.5 log 10 copies/ml in this analysis (FIG. 3B) and a significantly different mean VL determined by a Wilcoxon signed-rank test. These data indicate that VL values from DBS were in consistent agreement with plasma across multiple analyses, whereas DPS showed greater variability. PCR amplification and genotyping analysis were substantially reduced in DPS samples compared to DBS or plasma (Table 12), and HIVDR genotyping results from DBS were comparable to plasma at VL≥1,000 copies/ml. Overall, these results indicate that DBS can be used for surveys to monitor HIVDR prevention failure in resource-limited settings.

Several studies have demonstrated that DBS can effectively detect HIVDR mutations [55-65], yet only a few evaluated DBS from ART-experienced patients for HIVDR genotyping [58-64]. In these studies, a broad range of DBS amplification rates were demonstrated, ranging from 58% [59, 63] to 100% [64]. Several of these studies reported substantially higher amplification efficiency from samples with a higher VL [60, 61, 63]. Consistent with these studies, a 50% genotyping efficiency was observed for DBS in samples with a plasma VL<1,000 copies/ml, and 100% genotyping rate in DBS samples with a plasma VL≥1,000 copies/ml (Table 12). In addition, a 98.8% nucleotide identity between specimen types (Table 12) was observed, which is in agreement with previously reported values of 99.3% [60], 98.8% [61], and 97.9% [62], providing further evidence that DBS perform similarly to plasma specimens for HIVDR genotyping in patients on ART.

In contrast to previous studies demonstrating high concordance in HIVDR mutation profiles between plasma and DBS from ART-treated patients [60, 61, 63, 64], 10 out of 78 total mutations were detected in plasma but not in DBS (Table 13). The four discordant mutations present in plasma specimens with a VL≥1,000 copies/ml and absent in corresponding DBS were the result of base mixtures, indicating an increased sensitivity in plasma specimens compared to DBS to detect sub-dominant quasispecies of virus in early failing patients. This decreased sensitivity in genotyping observed in DBS could be the result of nucleic acid degradation during the prolonged storage of the specimens at ambient temperature, or due to decreased sample volume (equivalent to 60 µl of plasma) of the DBS specimens compared to plasma (200 µl). Conversely, it has been shown that newly acquired drug resistance mutations can be detected in plasma RNA before they could be detected in cell-associated proviral DNA [66], and therefore the absence of these mutations in DBS in this study could reflect a newly emerging drug-resistant quasispecies of virus. In this example, proviral DNA and RNA were not differentiated in DBS specimens and therefore it cannot be ruled out that the results were due to a contribution of proviral DNA. However the detection of 3 mutations in DBS that were not detected in plasma specimens (Table 13) indicates that proviral DNA may contribute to genotyping results from DBS. Previous studies showed that proviral DNA could contribute to HIVDR genotyping results when DBS were used [57, 61, 67], however this contribution did not significantly alter the overall resistance profiles [61] which is in agreement with the results herein. In this example, the majority of discordant mutations (6) between plasma and DBS occurred in specimens with a plasma VL<1,000 copies/ml (Table 13). Based on WHO recommendations, specimens with VL<1,000 copies/ml would not be genotyped in HIVDR monitoring surveys [4].

Unlike DBS, DPS performed poorly for genotyping. DPS have been shown to have reduced PCR amplification rates following 1 month at 20° C. [67], and even faster degradation at higher temperatures and humidity [67, 68]. The data herein demonstrate that DPS stored for prolonged periods at ambient temperature (median of 83.5 days) are not suitable for HIVDR analysis.

In summary, it is shown that DBS are comparable to plasma for VL and HIVDR analysis in ART-treated patients. DBS require less training to collect and do not require cold-chain transport, and can therefore be collected in more remote areas, increasing the sampling diversity at a decreased cost.

REFERENCES

1. Geretti A M (2007) Epidemiology of antiretroviral drug resistance in drug-naive persons. Curr Opin Infect Dis 20: 22-32.
2. Bennett D E (2006) The requirement for surveillance of HIV drug resistance within antiretroviral rollout in the developing world. Curr Opin Infect Dis 19: 607-614.
3. Bertagnolio S, Derdelinckx I, Parker M, Fitzgibbon J, Fleury H, et al. (2008) World Health Organization/HIVResNet Drug Resistance Laboratory Strategy. Antivir Ther 13 Suppl 2: 49-57.
4. Jordan M R, Bennett D E, Bertagnolio S, Gilks C F, Sutherland D (2008) World Health Organization surveys to monitor HIV drug resistance prevention and associated factors in sentinel antiretroviral treatment sites. Antivir Ther 13 Suppl 2: 15-23.
5. Bennett D E, Camacho R J, Otelea D, Kuritzkes D R, Fleury H, et al. (2008) World Health Organization surveys to monitor HIV drug resistance prevention and associated factors in sentinel antiretroviral treatment sites. PLoS One 13 Suppl 2: e4724.
6. Hirsch M S, Gunthard H F, Schapiro J M, Brun-Vezinet F, Clotet B, et al. (2008) Antiretroviral drug resistance testing in adult HIV-1 infection: 2008 recommendations of an International AIDS Society-USA panel. Top HIV Med 16: 266-285.
7. Gilks C F, Crowley S, Ekpini R, Gove S, Perriens J, et al. (2006) The WHO public-health approach to antiretroviral treatment against HIV in resource-limited settings. Lancet 368: 505-510.
8. Eshleman S H, Hackett J, Jr., Swanson P, Cunningham S P, Drews B, et al. (2004) Characterization of nevirapine resistance mutations in women with subtype A vs. D HIV-1 6-8 weeks after single-dose nevirapine (HIVNET 012). J Clin Microbiol 35: 126-130.
9. Jagodzinski L L, Cooley J D, Weber M, Michael N L (2003) Performance characteristics of human immunodeficiency virus type 1 (HIV-1) genotyping systems in sequence-based analysis of subtypes other than HIV-1 subtype B. J Clin Microbiol 41: 998-1003.
10. Saravanan S, Vidya M, Balakrishnan P, Kumarasamy N, Solomon S S, et al. (2009) Evaluation of two human immunodeficiency virus-1 genotyping systems: ViroSeq 2.0 and an in-house method. J Virol Methods 159: 211-216.
11. Schuurman R, Demeter L, Reichelderfer P, Tijnagel J, de Groot T, et al. (1999) Worldwide evaluation of DNA sequencing approaches for identification of drug resistance mutations in the human immunodeficiency virus type 1 reverse transcriptase. J Clin Microbiol 37: 2291-2296.
12. Aghokeng A F, Eitel Mpoidi-Ngole, Julius E. Chia, Elvine M. Edoul, Eric Delaporte, and Martine Peeters (2011) High failure rate of ViroSeq™ HIV-1 Genotyping System for drug resistance testing in Cameroon, a context of broad HIV-1 genetic diversity. J Clin Microbiol doi: 101128/JCM01478-10.
13. Beddows S, Galpin S, Kazmi S H, Ashraf A, Johargy A, et al. (2003) Performance of two commercially available sequence-based HIV-1 genotyping systems for the detection of drug resistance against HIV type 1 group M subtypes. J Med Virol 70: 337-342.
14. Fontaine E, Riva C, Peeters M, Schmit J C, Delaporte E, et al. (2001) Evaluation of two commercial kits for the detection of genotypic drug resistance on a panel of HIV type 1 subtypes A through J. J Acquir Immune Defic Syndr 28: 254-258.
15. Bennett D E, Bertagnolio S, Sutherland D, Gilks C F (2008) The World Health Organization's global strategy for prevention and assessment of HIV drug resistance. Antivir Ther 13 Suppl 2: 1-13.
16. Wallis C L, Papathanasopoulos M A, Lakhi S, Karita E, Kamali A, et al. Affordable in-house antiretroviral drug resistance assay with good performance in non-subtype B HIV-1. J Virol Methods 163: 505-508.
17. Eshleman S H, Hackett J, Jr., Swanson P, Cunningham S P, Drews B, et al. (2004) Performance of the Celera Diagnostics ViroSeq HIV-1 Genotyping System for sequence-based analysis of diverse human immunodeficiency virus type 1 strains. J Clin Microbiol 42: 2711-2717.
18. Grant R M, Hecht F M, Warmerdam M, Liu L, Liegler T, et al. (2002) Time trends in primary HIV-1 drug resistance among recently infected persons. JAMA 288: 181-188.
19. Hirsch M S, Brun-Vezinet F, Clotet B, Conway B, Kuritzkes D R, et al. (2003) Antiretroviral drug resistance testing in adults infected with human immunodeficiency virus type 1: 2003 recommendations of an International AIDS Society-USA Panel. Clin Infect Dis 37: 113-128.
20. Buckton A J (2008) New methods for the surveillance of HIV drug resistance in the resource poor world. Curr Opin Infect Dis 21: 653-658.
21. WHO (2010) WHO HIVDR Laboratory Guidance. wwwWHOint/hiv/topics/drugresistance, July 2010.
22. Yang C, A. McNulty, K. Diallo, J. Zhang, B. Titanji, S. Kassim, N. Wadonda-Kabondo, J. Aberle-Grasse, T. Kibuka, P. M. Ndumbe, S. Vedapuri, Z. Zhou, B. Chilima, and J. N. Nkengasong (2010) Development and application of a broadly sensitive dried-blood-spot-based genotyping assay for global surveillance of HIV-1 drug resistance. J Clin Microbiol 48: 3158-3164.
23. WHO (2010) WHO Manual for HIV drug resistance testing using dried blood spot specimens. wwwWHOint/hiv/topics/drugresistance.
24. Weidle P, J. Kiarie, P. Intalapaporn, J. Stringer, P. Muiruri, I. zulu, M. McConnell, C. Yang, O. Bolu, J. Johnson, and the NNRTI Response Study Team (2010) NVP resistance mutations among women exposed to a sdNVP intrapartum more than 1 year prior to starting NNRTI-based ART are not associated with virologic failure. 17th Conference on Retroviruses and Opportunistic Infections Abstract p 431, 2010, Sanfrancisco, Calif., USA.
25. McConnell M, T. jariyasethpong, N. Chantharojwong, C. Utenpitak, Z. Zhou, J-F. Li, J. McNicholl, O. Bolu, P. Weidle, and T. Anekthananon (2010) Low level HIV-1 viremia in Thai Women 24 weeks after treatment initiation with NNRTI-based ART was not associated with prior single-dose Nevirapine exposure or viral resistance mutations. 17th Conference on Retroviruses and Opportunistic Infections Abstract p 243, 2010, Sanfrancisco, Calif., USA.
26. Harrigan P R, Dong W, Wynhoven B, Mo T, Hall T, et al. Performance of ReCall basecalling software for high-throughput HIV drug resistance basecalling using "in-house" methods. The XIV international AIDS Conference, Barcelona, Spain, Jul. 7-12, 2002 Abstract #TuPeB4598.
27. Tamura K D J, Neil M, and Kumar S (2007) MEGA4: Molecular evolutionary genetics analysis software version 4.0. Mol Biol Evol 24: 1596-1599.
28. Bennett D E, Camacho R J, Otelea D, Kuritzkes D R, Fleury H, et al. (2009) Drug resistance mutations for surveillance of transmitted HIV-1 drug-resistance: 2009 update. PLoS One 4: e4724.
29. Hall T A (1999) BioEdit: a user-friendly biological sequence alignment editor and analysis program for windows 95/98/NT. Nucl Acids Symp Ser 41: 95-98.
30. de Oliveira T, K. Deforche, S. Cassol, M. Salminem, D. Paraskevis, C. Seebregts, J. Snoeck, E. J. van Rensburg, A. M. J. Wensing, D. A. van de Vijver, C. A. Boucher, R. Camacho, and A-M Vandamme. (2005) An automated genotyping system for analysis of HIV-1 and other microbial sequences. Bioinfomatics 21: 3797-3800.
31. Johnson J A, Li J F, Wei X, Lipscomb J, Irlbeck D, et al. (2008) Minority HIV-1 drug resistance mutations are present in antiretroviral treatment-naive populations and associate with reduced treatment efficacy. PLoS Med 5: e158.
32. Simen B B, Simons J F, Hullsiek K H, Novak R M, Macarthur R D, Baxter J D, Huang C, Lubeski C, Turenchalk G S, Braverman M S, Desany B, Rothberg J M, Egholm M, Kozal M J; Terry Beirn (2009) Low-abundance drug-resistant viral variants in chronically HIV-infected, antiretroviral treatment-naive patients significantly impact treatment outcomes. J Infect Dis 199: 693-701.
33. Goodenow M, Huet T, Saurin W, Kwok S, Sninsky J, et al. (1989) HIV-1 isolates are rapidly evolving quasispecies: evidence for viral mixtures and preferred nucleotide substitutions. J Acquir Immune Defic Syndr 2: 344-352.
34. Hearps A C, Ryan C E, Morris L M, Plate M M, Greengrass V, et al. Stability of dried blood spots for HIV-1 drug resistance analysis. Curr HIV Res 8: 134-140.
35. Kijak G H, Simon V, Balfe P, Vanderhoeven J, Pampuro S E, et al. (2002) Origin of human immunodeficiency virus type 1 quasispecies emerging after antiretroviral treatment interruption in patients with therapeutic failure. J Virol 76: 7000-7009.
36. Lira R, Valdez-Salazar H, Vazquez-Rosales G, Rojas-Montes O, Ruiz-Tachiquin M, et al. (2010) Genotypic testing for HIV-1 drug resistance using dried blood samples. Arch Virol 155: 1117-1125.
37. Parkin N T, J. Fitzgibbon, J. Bremer, and S. Bertagnolio. (2009) HIV drug resistance genotyping external quality assurance (EQA) for laboratories in the World Health Organization (WHO) resNet during 2007-2009. Antivir Ther 14 (suppl 1):A162.
38. Galli R A, Sattha B, Wynhoven B, O'Shaughnessy M V, Harrigan aPR (2003) Sources and Magnitude of Intralaboratory Variability in a Sequence-based Genotypic Assay for Human Immunodeficiency Virus Type 1 drug Resistance. Journal of Clinical Microbiology 41: 2900-2907.
39. Shafer R W H K, Zolopa A R, Warford A, Bloor S, Betts B J, Merigan T C, Harrigan R, Larder B A (2001) High degree of interlaboratory reproducibility of human immunodeficiency virus type 1 protease and reverse transcriptase sequencing of plasma samples from heavily treated patients. J Clin Microbiol 39: 1522-1529.
40. Chen J H, Wong K H, Chan K, Lam H Y, Lee S S, et al. (2007) Evaluation of an in-house genotyping resistance test for HIV-1 drug resistance interpretation and genotyping. J Clin Virol 39: 125-131.
41. Eshleman S H, Crutcher G, Petrauskene O, Kunstman K, Cunningham S P, et al. (2005) Sensitivity and specificity of the ViroSeq human immunodeficiency virus type 1 (HIV-1) genotyping system for detection of HIV-1 drug resistance mutations by use of an ABI PRISM 3100 genetic analyzer. J Clin Microbiol 43: 813-817.
42. Eshleman S H, Jones D, Flys T, Petrauskene O, Jackson J B (2004) Performance of the Celera Diagnostics ViroSeq HIV-1 Genotyping System for sequence-based analysis of diverse human immunodeficiency virus type 1 strains. Biotechniques 42: 2711-2717.
43. Eshleman S H, Mracna M, Guay L A, Deseyve M, Cunningham S, et al. (2001) Selection and fading of resistance mutations in women and infants receiving nevirapine to prevent HIV-1 vertical transmission (HIVNET 012). Aids 15: 1951-1957.
44. Mracna M, Becker-Pergola G, Dileanis J, Guay L A, Cunningham S, et al. (2001) Performance of Applied Biosystems ViroSeq HIV-1 Genotyping System for sequence-based analysis of non-subtype B human immunodeficiency virus type 1 from Uganda. J Clin Microbiol 39: 4323-4327.
45. Abegaz W E, Grossman Z, Wolday D, Ram D, Kaplan J, et al. (2008) Threshold survey evaluating transmitted HIV drug resistance among public antenatal clinic clients in Addis Ababa, Ethiopia. Antivir Ther 13 Suppl 2: 89-94.
46. Hallack R, Doherty L E, Wethers J A, Parker M M (2008) Evaluation of dried blood spot specimens for HIV-1 drug-resistance testing using the Trugene HIV-1 genotyping assay. J Clin Virol 41: 283-287.
47. Youngpairoj A S, Masciotra S, Garrido C, Zahonero N, de Mendoza C, et al. (2008) HIV-1 drug resistance genotyping from dried blood spots stored for 1 year at 4 degrees C. J Antimicrob Chemother 61: 1217-1220.
48. National AIDS/STDs Control Program FMoH. National Guideline for HIV and AIDS Treatment and Care in Adolescents and Adults. 2007.
49. Ugbena et al., Virological response and HIV-1 drug resistance development profile among patients treated with the first-line antiretroviral regimens in Nigeria. Submitted 2011.
50. Biomerieux. NucliSens EasyQ HIV-1 v1.1 RUO Package Insert.
51. Johannessen et al., *Clin Infect Dis* 2009 Sep. 15; 49(6): 976-81.
52. Zhou et al., PLoS One November 2011; 6(11).
53. Bland J M, Altman D G. Statistical methods for assessing agreement between two methods of clinical measurement. *Lancet* 1986, 1(8476):307-10.
54. Fleiss J L, ed. Statistical Methods for Rates and Proportions. 2nd ed. New York: John Wiley, 1981.
55. Bertagnolio et al., Antivir Ther 2007; 12(1):107-13.
56. Lira et al., Arch Virol 2010 July; 155(7):1117-25.
57. McNulty et al., J Clin Microbiol 2007; 45(2):517-21.
58. Yang et al., J Clin Microbiol 2010; 48(9):3158-64.
59. Garrido et al., J Antimicrob Chemother 2008; 61(3): 694-8.
60. Hallack et al., J Clin Virol 2008; 41(4):283-7.
61. Masciotra et al., AIDS 2007; 21(18):2503-11.
62. Steegen et al., J Clin Microbiol 2007; 45(10):3342-51.
63. Youngpairoj et al., J Antimicrob Chemother 2008; 61(6): 1217-20.
64. Ziemniak et al., *J Virol Methods* 2006; 136(1-2):238-47.
65. Buckton et al., J Antimicrob Chemother 2008; 62(6): 1191-8.
66. Kaye et al., AIDS Res Hum Retroviruses 1995; 11(10): 1221-5.

67. Monleau et al., J Antimicrob Chemother 2010; 65(8): 1562-6.
68. Garcia-Lerma et al., J Antimicrob Chemother 2009; 64(1):33-6

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A degenerate oligonucleotide consisting of the nucleic acid of SEQ ID NO: 1, 2, 3, 5, 7, 8, or 9, and a label attached to the degenerate oligonucleotide, and wherein the label is a radioactive isotope, ligand, chemiluminescent agent, fluorophore, hapten, enzyme, or combination thereof.

2. A kit comprising:
one or more of the degenerate oligonucleotides of claim 1; and
one or more reagents for isolating RNA, one or more reagents for performing reverse transcription, one or more reagents for performing reverse transcription polymerase chain reaction (RT-PCR), one or more reagents for sequencing a nucleic acid molecule, or a combination thereof.

3. The kit of claim 2, further comprising an oligonucleotide consisting of the nucleic acid sequence shown in SEQ ID NO: 4, 6 or 10.

4. The kit of claim 2, further comprising materials for collecting a blood sample, determining an HIV-1 viral load, or combinations thereof.

5. The kit of claim 2, wherein the kit comprises:
the degenerate oligonucleotide of SEQ ID NO: 1;
the degenerate oligonucleotides of SEQ ID NOS: 1 and 2, and the oligonucleotide of SEQ ID NO: 4;
the degenerate oligonucleotide of SEQ ID NO: 5 and the oligonucleotide of SEQ ID NO: 6;
the degenerate oligonucleotides of SEQ ID NOS: 1, 2, and 3;
the degenerate oligonucleotides of SEQ ID NOS: 1, 2, and 3 and the oligonucleotide of SEQ ID NO: 4;
the oligonucleotides of SEQ ID NOS: 4, 6, and 10 and the degenerate oligonucleotides of SEQ ID NOS: 5, 7, 8 and 9; or
the oligonucleotides of SEQ ID NOS: 4, 6, and 10 and the degenerate oligonucleotides of SEQ ID NOS: 1, 2, 3, 5, 7, 8 and 9.

6. The kit of claim 5, wherein the kit comprises the degenerate oligonucleotide of SEQ ID NO: 5 and the oligonucleotide of SEQ ID NO: 6.

7. The kit of claim 5, wherein the kit comprises the oligonucleotides of SEQ ID NOS: 6, and 10 and the degenerate oligonucleotides of SEQ ID NOS: 5, 7, 8 and 9.

8. The kit of claim 2, wherein the kit comprises the oligonucleotides of SEQ ID NOS: 6 and 10 and the degenerate oligonucleotides of SEQ ID NOS: 1, 5, 7, 8 and 9.

9. The kit of claim 2, wherein the kit comprises DNA polymerase.

10. The kit of claim 2, wherein the kit comprises dNTPs.

11. A degenerate oligonucleotide comprising the nucleic acid sequence of SEQ ID NO: 1, 2, 3, 5, 7, 8, or 9 and a label attached to the degenerate oligonucleotide, and wherein the label is a radioactive isotope, ligand, chemiluminescent agent, fluorophore, hapten, enzyme, or combination thereof.

12. A kit comprising:
one or more of the degenerate oligonucleotides of claim 11; and
one or more reagents for isolating RNA, one or more reagents for performing reverse transcription, one or more reagents for performing reverse transcription polymerase chain reaction (RT-PCR), one or more reagents for sequencing a nucleic acid molecule, or a combination thereof.

13. The kit of claim 12, further comprising an oligonucleotide consisting of the nucleic acid sequence shown in SEQ ID NO: 4, 6 or 10.

14. The kit of claim 12, wherein the kit comprises:

the degenerate oligonucleotides of SEQ ID NOS: 1, 2, and 3;

the degenerate oligonucleotides of SEQ ID NOS: 1, 2, and 3 and the oligonucleotide of SEQ ID NO:4;

the oligonucleotides of SEQ ID NOS: 6 and 10 and the degenerate oligonucleotides of SEQ ID NOS: 5, 7, 8 and 9;

the oligonucleotides of SEQ ID NOS: 4, 6, and 10 and the degenerate oligonucleotides of SEQ ID NOS: 5, 7, 8 and 9; or the oligonucleotides of SEQ ID NOS: 4, 6, and 10 and the degenerate oligonucleotides of SEQ ID NOS: 1, 2, 3, 5, 7, 8 and 9.

15. A kit comprising:

the degenerate oligonucleotides of SEQ ID NOS: 1, 2, 3, and 5; and the oligonucleotides of SEQ ID NO: 4 and 6.

16. The kit of claim 15, further comprising:

the oligonucleotide of SEQ ID NO: 10; and the degenerate oligonucleotides of SEQ ID NOS: 7, 8 and 9.

17. The kit of claim 16, further comprising: one or more reagents for isolating RNA, one or more reagents for performing reverse transcription, one or more reagents for performing reverse transcription polymerase chain reaction (RT-PCR), one or more reagents for sequencing a nucleic acid molecule, or a combination thereof.

18. The kit of claim 16, wherein the kit further comprises a DNA polymerase, dNTPs, or both.

19. The kit of claim 15, further comprising:

one or more reagents for isolating RNA, one or more reagents for performing reverse transcription, one or more reagents for performing reverse transcription polymerase chain reaction (RT-PCR), one or more reagents for sequencing a nucleic acid molecule, or a combination thereof.

\* \* \* \* \*